(12) United States Patent
Roughton et al.

(10) Patent No.: US 8,211,927 B2
(45) Date of Patent: Jul. 3, 2012

(54) 5-PHENYL-ISOXAZOLE-3-CARBOXAMIDE DERIVATIVES AS TRPV1 MODULATORS

(75) Inventors: Andrew Laird Roughton, Toronto (CA); Koc-Kan Ho, West Windsor, NJ (US); Michael Ohlmeyer, Plainsboro, NJ (US); Irina Neagu, Belmont, MA (US); Steven G. Kultgen, Salt Lake City, UT (US); Nasrin Ansari, Monmouth Junction, NJ (US); Yajing Rong, Yardley, PA (US); Paul David Ratcliffe, Newhouse (GB); Ronald Palin, Newhouse (GB)

(73) Assignee: MSD, Oss B.V., Oss (NL)

( * ) Notice: Subject to any disclaimer, the term of this patent is extended or adjusted under 35 U.S.C. 154(b) by 0 days.

(21) Appl. No.: 12/671,113

(22) PCT Filed: Jul. 31, 2008

(86) PCT No.: PCT/EP2008/060090
§ 371 (c)(1),
(2), (4) Date: Nov. 29, 2010

(87) PCT Pub. No.: WO2009/016241
PCT Pub. Date: Feb. 5, 2009

(65) Prior Publication Data
US 2011/0065764 A1    Mar. 17, 2011

Related U.S. Application Data

(60) Provisional application No. 60/953,493, filed on Aug. 2, 2007, provisional application No. 61/013,700, filed on Dec. 14, 2007.

(51) Int. Cl.
*A61K 31/42* (2006.01)
*C07D 261/18* (2006.01)

(52) U.S. Cl. ........................................ 514/378; 548/248
(58) Field of Classification Search .................. 514/378; 548/248
See application file for complete search history.

(56) References Cited

OTHER PUBLICATIONS

Dal Piaz et al., 4,5-Disubstituted-3-carboethoxyisoxazoles. II. Hydrolysis and derivatives, 1968, Gazzetta Chimica Italiana, 98 (5), pp. 667-680.*

* cited by examiner

*Primary Examiner* — Kamal Saeed
*Assistant Examiner* — Kristin Bianchi
(74) *Attorney, Agent, or Firm* — Sylvia A. Ayler; Gerard M. Devlin

(57) ABSTRACT

The present invention relates to isoxazole-3-carboxamide derivative having the general Formula (I), or a pharmaceutically acceptable salt thereof, to pharmaceutical compositions comprising the same, as well as to the use of said isoxazole-3-carboxamide derivatives for the treatment of TRPV1 mediated disorders, such as acute and chronic pain disorders, acute and chronic neuropathic pain, acute and chronic inflammatory pain, respiratory diseases, and lower urinary tract disorders.

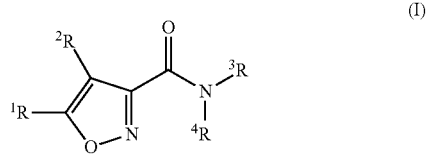

(I)

13 Claims, No Drawings

5-PHENYL-ISOXAZOLE-3-CARBOXAMIDE DERIVATIVES AS TRPV1 MODULATORS

CROSS REFERENCE TO RELATED APPLICATION

This application is entered into national stage examination under 37 U.S.C. 371 and stems from international patent application No. PCT/EP2008/060090 filed on Jul. 31, 2008, which claims priority from application Nos. U.S. 60/953,493 filed on Aug. 2, 2007 and U.S. 61/013,700 filed on Dec. 14, 2007.

FIELD OF THE INVENTION

The present invention relates to isoxazole-3-carboxamide derivatives, to pharmaceutical compositions comprising the same and to the use of these isoxazole-3-carboxamide derivatives in the treatment of TRPV1 related disorders.

BACKGROUND OF THE INVENTION

The vanilloid receptor (VR1 or TRPV1), a non-selective ligand-gated cation channel belonging to the Transient Receptor Channel family (TRP family) of cation channels, is highly expressed on the peripheral termini of small diameter sensory neurones innervating many tissues including skin, bladder, airway and gastrointestinal tract. More specifically TRPV1 receptors are located on a subset Aδ and C fibres, the afferents commonly associated with nociception (Mezey et al., Proc. Natl. Acad. Sci. 97, 3655-3660, 2000). Characterisation of this channel at the molecular level identified it as the target of the vanilloid capsaicin, the main pungent constituent of hot chili peppers (Caterina et al., Nature 389, 816-824, 1997). Indeed, sensitivity to capsaicin has been used for many years as a marker of nociceptor activity. These, polymodal nociceptors are activated by multiple noxious stimuli including chemical, mechanical and thermal. Study of the functional properties of TRPV1 demonstrated that this receptor shares many properties common to nociceptors including activation by thermal stimuli (>43° C.) and chemicals (including capsaicin and endovanilloids such as N-arachidonoyl-dopamine (NADA) and lipoxygenase metabolites), as well as sensitisation and activation by acidification. Furthermore, inflammatory mediators (including ATP and bradykinin) have been shown to functionally sensitise TRPV1 in vitro. This evidence suggests that TRPV1 has an integral role in the polymodal detection of noxious stimuli and contributes to the transduction of inflammatory pain responses and potentially also peripheral tissue injury (reviewed in Di Marzo et al., Curr. Opin. Neurobiol. 12, 372-379, 2002).

A role for TRPV1 in the detection of painful stimuli is also inferred from data in gene knockout mice. Mice null for TRPV1 show attenuated development of behavioural thermal hyperalgesia after an inflammatory insult (Caterina et al., Science 288, 306-313, 2000, Davis et al., Nature 405, 183-187, 2000). Small diameter sensory neurones from these animals also show altered responses to thermal and acid stimuli. Moreover, altered expression and/or functional activity of TRPV1 has been demonstrated following inflammation and nerve injury in animals models (Amaya et al., Brian Res. 963, 190-196, 2003, Rashid et al., J. Pharm. Exp. Ther. 304, 940-948, 2003, Hong & Wiley, J. Biol. Chem. 280, 618-627, 2005).

In addition, to a role in pain transduction there is also growing evidence for a role for TRPV1 in regulating afferent and efferent function of sensory nerves and the function of non-neuronal cells. Indeed, altered bladder function, with a higher frequency of low amplitude, non-voiding bladder contractions and an increase in bladder capacity has been observed by in TRPV1 KO mice (Birder et al., Nat. Neurosci. 5, 856-860, 2002). This may involve neuronal TRPV1 and TRPV1 expressed on uroepithelial cells. Thus, there is clear evidence to suggest that agents modulating TRPV1 activity will have utility in not only in pain states and other diseases involving inflammation but also in conditions involving hyperactivity of primary sensory fibres (e.g. bladder overactivity and urge incontinence).

Isoxazole-3-carboxamide derivatives have been disclosed in the International Patent Application WO 2007/067710 (Amphora Discovery Corporation) as modulators of the TRPV1 receptor and useful in the treatment of TRPV1 mediated disorders, such as in the treatment of acute and chronic pain disorders, acute and chronic neuropathic pain, acute and chronic inflammatory pain, respiratory diseases, and lower urinary tract disorders.

There remains a need for additional, more potent, compounds that are useful in the treatment of TRPV1 mediated disorders.

DETAILED DESCRIPTION OF THE INVENTION

To this end the present invention provides isoxazole-3-carboxamide derivatives having the general Formula I

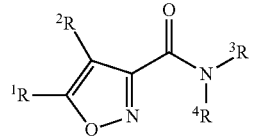

Formula 1 wherein
$R_1$ is phenyl, pyridyl or pyrazolyl, each of which optionally substituted by 1-3 substituents selected from halogen, $(C_{1-4})$alkyl and $(C_{1-4})$alkyloxy, the alkyl and alkyloxy group being optionally substituted with halogen;
$R_2$ is $(C_{1-3})$alkyl, $(C_{3-8})$cycloalkyl, cyano or halogen;
$R_3$ is $(C_{1-8})$alkyl, $(C_{2-8})$alkenyl, or $(C_{2-8})$alkynyl, each of which optionally substituted by one or 2 substituents independently selected from halogen, hydroxy and phenyl, optionally substituted by hydroxy or amino; or
$R_3$ is $(C_{3-10})$cycloalkyl, $(C_{3-8})$cycloalkenyl or $(C_{3-8})$cycloalkyl$(C_{1-3})$alkyl, each cycloalkyl group may be fused to a benzo group, and each cycloalkyl group may be substituted by oxo, hydroxyimino, amino, hydroxy, carboxy, cyano, $(C_{1-3})$alkyl or hydroxy$(C_{1-3})$alkyl; or
$R_3$ is a saturated 4-8-membered heterocyclic ring containing 1 or 2 heteroatoms selected from $NR_5$, O, S and $SO_2$, optionally substituted by hydroxyl or oxo; or
$R_3$ is phenyl, naphthyl or pyridyl, each of which may be fused to a 5- or 6-membered saturated heterocyclic ring containing 1 or 2 heteroatoms selected from $NR_5$, O and S, and each of which may be substituted by amino, halogen, hydroxy, hydroxyimino, oxo, mercapto, $(C_{1-3})$-alkyl, $(C_{1-3})$-alkyloxy or hydroxy$(C_{1-3})$alkyl, each alkyl group optionally substituted by one or more halogens; or
$R_3$ is a bicyclic heteroaromatic ring system containing 1-3 heteroatoms selected from N, O and S, which may be substituted by hydroxy, amino, $(C_{1-3})$alkyl or hydroxy-$(C_{1-3})$alkyl;
$R_4$ is H or $(C_{1-4})$alkyl; or $R_4$ together with $R_3$ and the N to which they are bonded form a saturated 4-8 membered ring, optionally containing a further heteroatom selected from O, S and $SO_2$, the ring being optionally substituted by oxo, hydroxyimino, amino, hydroxy, carboxy, carboxamido, $(C_{1-3})$alkyl, hydroxy$(C_{1-3})$ alkyl, $(C_{1-3})$-alkyloxy; $(C_{1-4})$alkylcarbonylamino or hydroxyl$(C_{1-3})$alkylaminocarbonyl;

$R_5$, where present, is H, $(C_{1-4})$alkyl, $(C_{1-4}$alkylcarbonyl or $(C_{1-4})$alkyloxycarbonyl; or a pharmaceutically acceptable salt thereof, with the proviso that N,N-dimethyl-4-bromo-5-phenylisoxazole-3-carboxamide and N,N-diethyl-4-cyano-5-phenylisoxazole-3-carboxamide are excluded.

The isoxazole-3-carboxamide derivatives for which no protection per se is sought relates to the disclosures of N,N-dimethyl-4-bromo-5-phenylisoxazole-3-carboxamide by Li, G. et al (Tet. Lett. 48, (26), 4595-4599, 2007) and of N,N-diethyl-4-cyano-5-phenylisoxazole-3-carboxamide by Dal Piaz, V. and Renzi, G. (Gazz. Chim. Ital. 98, 667-680, 1968), wherein these isoxazole-3-carboxamide derivatives are described as synthetic intermediates, without any pharmacological activity.

In one embodiment the present invention provides isoxazole-3-carboxamide derivatives having the general Formula I wherein $R_1$ is phenyl or pyridyl, optionally substituted by 1-3 substituents selected from halogen, $(C_{1-4})$alkyl and $(C_{1-4})$alkyloxy, the alkyl and alkyloxy group being optionally substituted with halogen;

$R_2$ is $(C_{1-3})$alkyl, $(C_{3-8})$cycloalkyl, cyano or halogen;

$R_3$ is $(C_{1-8})$alkyl, $(C_{2-8})$alkenyl, or $(C_{2-8})$alkynyl, each of which optionally substituted by halogen, hydroxy or phenyl; or $R_3$ is $(C_{3-10})$cycloalkyl, $(C_{3-8})$cycloalkenyl or $(C_{3-8})$cycloalkyl$(C_{1-3})$alkyl, each cycloalkyl group may be fused to a benzo group, and each cycloalkyl group may be substituted by oxo, hydroxyimino, hydroxy, carboxy, cyano, $(C_{1-3})$alkyl and hydroxy$(C_{1-3})$alkyl; or $R_3$ is a saturated 4-8-membered heterocyclic ring containing 1 or 2 heteroatoms selected from N, O, S and $SO_2$, optionally substituted by hydroxyl or oxo; or $R_3$ is phenyl or pyridyl, each of which may be fused to a 5- or 6-membered saturated heterocyclic ring containing 1 or 2 heteroatoms selected from $NR_5$, O and S, and each of which may be substituted by amino, halogen, hydroxy, hydroxyimino, oxo, mercapto, $(C_{1-3})$-alkyl, $(C_{1-3})$-alkyloxy or hydroxy$(C_{1-3})$alkyl, each alkyl group optionally substituted by one or more halogens; or $R_3$ is a bicyclic heteroaromatic ring system containing 1-3 heteroatoms selected from N, O and S, which may be substituted by hydroxy, amino, $(C_{1-3})$alkyl or hydroxy-$(C_{1-3})$alkyl;

$R_4$ is H or $(C_{1-4})$alkyl; or $R_4$ together with $R_3$ and the N to which they are bonded form a saturated 4-8 membered ring, optionally containing a further heteroatom selected from O, S and $SO_2$, the ring being optionally substituted by oxo, hydroxyimino, hydroxy, carboxy, carboxamido, $(C_{1-3})$alkyl, or hydroxy$(C_{1-3})$alkyl or $(C_{1-3})$-alkyloxy;

$R_5$, where present, is H, $(C_{1-4})$alkyl or $(C_{1-4})$alkyloxycarbonyl; or a pharmaceutically acceptable salt thereof, with the proviso that N,N-dimethyl-4-bromo-5-phenylisoxazole-3-carboxamide and N,N-diethyl-4-cyano-5-phenylisoxazole-3-carboxamide are excluded.

In a further embodiment the present invention provides isoxazole-3-carboxamide derivatives having the general Formula I

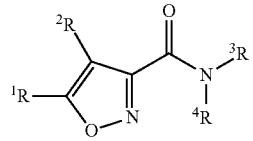

Formula 1 wherein $R_1$ is phenyl or pyridyl, optionally substituted by 1-3 substituents selected from halogen, $(C_{1-4})$alkyl and $(C_{1-4})$alkyloxy, the alkyl and alkyloxy group being optionally substituted with halogen;

$R_2$ is $(C_{1-3})$alkyl, $(C_{3-8})$cycloalkyl, cyano or halogen;

$R_3$ is $(C_{1-8})$alkyl, $(C_{2-8})$alkenyl, or $(C_{2-8})$alkynyl, each of which optionally substituted by halogen, hydroxy or phenyl; or $R_3$ is $(C_{3-10})$cycloalkyl, $(C_{3-8})$cycloalkenyl or $(C_{3-8})$cycloalkyl$(C_{1-3})$alkyl, each cycloalkyl group may be fused to a benzo group, and each cycloalkyl group may be substituted by oxo, hydroxyimino, hydroxy, carboxy, cyano, $(C_{1-3})$alkyl and hydroxy$(C_{1-3})$alkyl; or $R_3$ is a saturated 4-8-membered heterocyclic ring containing 1 or 2 heteroatoms selected from N, O, S and $SO_2$, optionally substituted by hydroxy; or $R_3$ is phenyl or pyridyl, each of which may be fused to a 5- or 6-membered saturated heterocyclic ring containing 1 or 2 heteroatoms selected from $NR_S$, O and S, and each of which may be substituted by amino, hydroxy, hydroxyimino, oxo, mercapto, $(C_{1-3})$-alkyl, $(C_{1-3})$-alkyloxy or hydroxy$(C_{1-3})$alkyl; or $R_3$ is a bicyclic heteroaromatic ring system containing 1-3 heteroatoms selected from N, O and S, which may be substituted by hydroxy, amino, $(C_{1-3})$alkyl or hydroxy-$(C_{1-3})$alkyl;

$R_4$ is H or $(C_{1-4})$alkyl; or $R_4$ together with $R_3$ and the N to which they are bonded form a saturated 4-8 membered ring, optionally containing a further heteroatom selected from O, S and $SO_2$, the ring being optionally substituted by oxo, hydroxyimino, hydroxy, carboxy, carboxamido, $(C_{1-3})$alkyl, or hydroxy$(C_{1-3})$alkyl or $(C_{1-3})$-alkyloxy;

$R_5$, where present, is H, $(C_{1-4})$alkyl or $(C_{1-4})$alkyloxycarbonyl; or a pharmaceutically acceptable salt thereof, with the proviso that N,N-dimethyl-4-bromo-5-phenylisoxazole-3-carboxamide and N,N-diethyl-4-cyano-5-phenylisoxazole-3-carboxamide are excluded.

The term $(C_{1-3})$alkyl used in the definition of Formula I means a branched or unbranched alkyl group having 1-3 carbon atoms, like propyl, isopropyl, ethyl and methyl. The term hydroxy$(C_{1-3})$alkyl means a branched or unbranched alkyl group having 1-3 carbon atoms substituted by 1 or 2 hydroxy groups, such as 3-hydroxypropyl, 2,3-dihydroxypropyl, 2-hydroxyethyl or hydroxymethyl.

The term $(C_{1-4})$alkyl as used in the definition of Formula I means a branched or unbranched alkyl group having 1-4 carbon atoms, like butyl, isobutyl, tertiary butyl, propyl, isopropyl, ethyl and methyl.

In the term $(C_{1-4})$alkyloxy, $(C_{1-4})$alkyl has the meaning as defined above.

Likewise, the term $(C_{1-8})$alkyl as used in the definition of Formula I means a branched or unbranched alkyl group having 1-8 carbon atoms, like octyl, heptyl, hexyl, pentyl, isopentyl, butyl, isobutyl, tertiary butyl, propyl, isopropyl, ethyl and methyl.

The term (C$_{2-8}$)alkenyl means a branched or unbranched alkenyl group having 2-8 carbon atomes, such as ethenyl, propen-2-yl, 2-methyl-propenyl, penten-4-yl and the like.

The term (C$_{2-8}$)alkynyl means a branched or unbranched alkynyl group having 2-8 carbon atomes, such as ethynyl, propyn-2-yl, pentyn-4-yl and the like.

The term (C$_{3-10}$)cycloalkyl means a cycloalkyl group having 3-10 carbon atoms, like cycloheptyl, cyclohexyl, cyclopentyl, cyclobutyl and cyclopropyl. Also included in this term are bicyclic cycloalkyl groups such as bicyclo[2,2,1]heptan-2-yl, bicyclo[2,2,1]hept-2-enyl, bicyclo[2,2,2]oct-5-enyl, and tricyclic alkyl groups such as adamantyl and the like.

The term (C$_{3-8}$)cycloalkenyl means a cycloalkenyl group having 3-8 carbon atoms, like cyclooct-3-yl, cyclohept-3-yl, cyclohex-3-yl and cyclopent-2-yl.

Each cycloalkyl ring may be fused to a benzo group to form a bicyclic ring system such as indan-1-yl, indan-2-yl, 1,2,3,4-tetrahydronaphth-1-yl and, 1,2,3,4-tetrahydronaphth-2-yl and the like. The benzo group may be substituted by hydroxyl, hydroxyl(C$_{1-3}$)alkyl or (C$_{1-3}$)alkyloxy.

The term a saturated 4-8-membered heterocyclic ring containing 1 or 2 heteroatoms selected from N, O, S and SO$_2$, as used in the definition of R$_3$ of formula I is exemplified by tetrahydropyranyl, tetrahydrofuranyl, tetrahydrothiopyranyl, tetrahydrothienyl and N-morpholinyl.

The term a bicyclic heteroaromatic ring system containing 1-3 heteroatoms selected from N, O and S, as used in the definition of R$_3$ of formula I is exemplified by as quinolyl, isoquinolyl, indolyl, indolizinyl, indazolyl, quinazolinyl, quinoxalinyl, cinnolinyl, benzothienyl, isobenzofuranyl and the like.

The term halogen means F, Cl, Br or I.

Preferred in the invention are those isoxazole-3-carboxamide derivatives according to formula I wherein R$_1$ is phenyl, and especially those wherein this phenyl group is substituted by fluoro, chloro, or CF$_3$ or a combination of these.

Further preferred are the compounds wherein R$_2$ is halogen, especially Cl and F.

Also preferred are the derivatives of formula I wherein R$_3$ is tetrahydropyranyl or (C$_{5-6}$)cycloalkyl, substituted by hydroxy or hydroxymethyl.

Specifically preferred isoxazole-3-carboxamide derivatives of the invention are:

4-Chloro-5-(4-(trifluoromethyl)phenyl)-N-(3-hydroxyphenyl)isoxazole-3-carboxamide;
4-Chloro-5-(4-chlorophenyl)-N-((1R,3S)-3-hydroxycyclohexyl)isoxazole-3-carboxamide;
4-Chloro-5-(3,4-difluorophenyl)-N-((1R,3S)-3-hydroxycyclohexyl)isoxazole-3-carboxamide;
4-Cyano-N-cyclopentyl-5-(4-(trifluoromethyl)phenyl)isoxazole-3-carboxamide;
4-Chloro-N-((1R,3S)-3-hydroxycyclopentyl)-5-(4-(trifluoromethyl)phenyl) isoxazole-3-carboxamide;
4-Chloro-N-((1R,3S)-3-hydroxycyclohexyl)-5-(4-(trifluoromethyl)phenyl) isoxazole-3-carboxamide;
4-Fluoro-N-((1R,3S)-3-hydroxycyclohexyl)-5-(4-(trifluoromethyl)phenyl) isoxazole-3-carboxamide;
4-Chloro-5-(4-chloro-3-fluorophenyl)-N-((1R,3S)-3-hydroxycyclohexyl) isoxazole-3-carboxamide;
4-Chloro-N-cyclopentyl-5-(4-(trifluoromethyl)phenyl)isoxazole-3-carboxamide;
4-Chloro-5-(4-chloro-3-fluorophenyl)-N-((1R,2S)-2-(hydroxymethyl)cyclohexyl) isoxazole-3-carboxamide;
4-Chloro-N-((1S,2R,3S,4R)-3-(hydroxymethyl)bicyclo [2.2.1]heptan-2-yl)-5-(4-(trifluoromethyl)phenyl)isoxazole-3-carboxamide;
4-Bromo-N-(tetrahydro-2H-pyran-4-yl)-5-(4-(trifluoromethyl)phenyl)isoxazole-3-carboxamide;
4-Chloro-N-(tetrahydro-2H-pyran-4-yl)-5-(4-(trifluoromethyl)phenyl)isoxazole-3-carboxamide;
4-Bromo-N-cyclopentyl-5-(4-(trifluoromethyl)phenyl)isoxazole-3-carboxamide;
4-Chloro-N-((1S,2R)-2-(hydroxymethyl)cyclohexyl)-5-(4-(trifluoromethyl)phenyl)isoxazole-3-carboxamide;
4-Chloro-N-((1S,3R)-3-hydroxycyclopentyl)-5-(4-(trifluoromethyl)phenyl) isoxazole-3-carboxamide;
(R)-4-Chloro-N-(3-(hydroxyimino)cyclopentyl)-5-(4-(trifluoromethyl)phenyl) isoxazole-3-carboxamide, cis/trans mix;
Racemic-4-Chloro-N-(cis-2-hydroxycyclohexyl)-5-(4-(trifluoromethyl)phenyl) isoxazole-3-carboxamide;
4-Chloro-5-(4-chloro-3-fluorophenyl)-N-((1R,3S)-3-hydroxycyclopentyl) isoxazole-3-carboxamide;
4-Fluoro-N-((1R,3S)-3-hydroxycyclopentyl)-5-(4-(trifluoromethyl)phenyl) isoxazole-3-carboxamide;
4-Chloro-5-(4-chlorophenyl)-N-((1R,3S)-3-hydroxycyclopentyl)isoxazole-3-carboxamide;
Racemic-cis-4-Chloro-N-(3-hydroxy-6-methoxy-2,3-dihydro-1H-inden-1-yl)-5-(4-(trifluoromethyl)phenyl)isoxazole-3-carboxamide;
4-Chloro-N-(tetrahydro-2H-pyran-3-yl)-5-(4-(trifluoromethyl)phenyl)isoxazole-3-carboxamide;
5-(4-Chlorophenyl)-4-fluoro-N-((1R,3S)-3-hydroxycyclohexyl)isoxazole-3-carboxamide;
(R)-4-Chloro-N-(3-oxocyclopentyl)-5-(4-(trifluoromethyl) phenyl)isoxazole-3-carboxamide;
4-Chloro-N-cyclobutyl-5-(4-(trifluoromethyl)phenyl)isoxazole-3-carboxamide;
4-Methyl-N-(tetrahydro-2H-pyran-4-yl)-5-(4-(trifluoromethyl)phenyl)isoxazole-3-carboxamide;
4-Chloro-N-cyclohexyl-5-(4-(trifluoromethyl)phenyl)isoxazole-3-carboxamide;
4-Chloro-N-((1R,4R)-4-methylcyclohexyl)-5-(4-(trifluoromethyl)phenyl) isoxazole-3-carboxamide;
N-Cyclopentyl-4-methyl-5-(4-(trifluoromethyl)phenyl) isoxazole-3-carboxamide;
4-Chloro-5-(4-chloro-3-fluorophenyl)-N-((1R,3S)-3-hydroxycyclohexyl) isoxazole-3-carboxamide;
Racemic-4-Chloro-N-(cis-2-hydroxycyclohexyl)-5-(4-(trifluoromethyl)phenyl)-isoxazole-3-carboxamide;
cis-4-Chloro-N-(4-hydroxycyclohexyl)-5-(4-(trifluoromethyl)phenyl)isoxazole-3-carboxamide;
N-Cyclopentyl-4-propyl-5-(4-(trifluoromethyl)phenyl)isoxazole-3-carboxamide;
N-Cyclopentyl-4-ethyl-5-(4-(trifluoromethyl)phenyl)isoxazole-3-carboxamide;
4-Chloro-5-(4-chlorophenyl)-N-cyclopentylisoxazole-3-carboxamide;
(S)-4-Chloro-N-(3-methylbutan-2-yl)-5-(4-(trifluoromethyl)phenyl)isoxazole-3-carboxamide;
4-Chloro-5-(3-fluoro-4-(trifluoromethyl)phenyl)-N-(tetrahydro-2H-pyran-4-yl)isoxazole-3-carboxamide;
4-Chloro-5-(3-fluoro-4-(trifluoromethyl)phenyl)-N-(tetrahydro-2H-pyran-4-yl)isoxazole-3-carboxamide;
4-Chloro-5-(3-fluoro-4-(trifluoromethyl)phenyl)-N-(3-(hydroxymethyl)phenyl) isoxazole-3-carboxamide;
4-Chloro-5-(3-fluoro-4-(trifluoromethyl)phenyl)-N-(2-(2-hydroxyethyl)phenyl) isoxazole-3-carboxamide;
(R)-4-Chloro-5-(3-fluoro-4-(trifluoromethyl)phenyl)-N-(1-hydroxybutan-2-yl)isoxazole-3-carboxamide;
(R)-4-Chloro-5-(3-fluoro-4-(trifluoromethyl)phenyl)-N-(1-hydroxy-3-methylbutan-2-yl)isoxazole-3-carboxamide;

4-Chloro-5-(3-fluoro-4-(trifluoromethyl)phenyl)-N-((1R, 3S)-3-hydroxycyclohexyl)isoxazole-3-carboxamide;
cis-4-Chloro-5-(3-fluoro-4-(trifluoromethyl)phenyl)-N-(4-hydroxycyclohexyl) isoxazole-3-carboxamide;
4-Chloro-5-(4-chlorophenyl)-N-cyclohexylisoxazole-3-carboxamide;
4-Chloro-5-(4-chlorophenyl)-N-cyclobutylisoxazole-3-carboxamide;
5-(4-tert-Butylphenyl)-4-chloro-N-cyclopentylisoxazole-3-carboxamide;
5-(4-tert-Butylphenyl)-4-chloro-N-(cis-4-hydroxycyclohexyl)isoxazole-3-carboxamide;
5-(4-tert-Butylphenyl)-4-chloro-N-((1S,2R)-2-(hydroxymethyl)cyclohexyl)-isoxazole-3-carboxamide;
5-(4-tert-Butylphenyl)-4-chloro-N-(tetrahydro-2H-pyran-4-yl)isoxazole-3-carboxamide;
5-(4-tert-Butylphenyl)-4-chloro-N-cyclobutylisoxazole-3-carboxamide 2,2,2-trifluoroacetate;
5-(4-tert-Butylphenyl)-4-chloro-N-isopropylisoxazole-3-carboxamide 2,2,2-trifluoroacetate;
(S)-4-Chloro-5-(4-(trifluoromethyl)phenyl)-N-(1,1,1-trifluoropropan-2-yl)isoxazole-3-carboxamide;
(R)—N-sec-Butyl-4-chloro-5-(4-(trifluoromethyl)phenyl) isoxazole-3-carboxamide;
4-Chloro-N-(cyclobutylmethyl)-5-(4-(trifluoromethyl)phenyl)isoxazole-3-carboxamide;
4-Chloro-N-(2-cyclopropylethyl)-5-(4-(trifluoromethyl)phenyl)isoxazole-3-carboxamide;
4-Chloro-N-(1,1,1-trifluorobutan-2-yl)-5-(4-(trifluoromethyl)phenyl)isoxazole-3-carboxamide;
4-Chloro-N-(3,3-difluorocyclobutyl)-5-(4-(trifluoromethyl)phenyl)isoxazole-3-carboxamide;
5-(4-Chloro-2-ethoxyphenyl)-N-((1R,2S)-2-hydroxycyclohexyl)-4-methyl-isoxazole-3-carboxamide;
5-(3-Fluoro-4-(trifluoromethyl)phenyl)-4-methyl-N-(tetrahydro-2H-pyran-4-yl)isoxazole-3-carboxamide;
5-(3-Fluoro-4-(trifluoromethyl)phenyl)-N-((1R,3S)-3-hydroxycyclohexyl)-4-methylisoxazole-3-carboxamide;
5-(3-Fluoro-4-(trifluoromethyl)phenyl)-N-(2-hydroxyethyl)-4-methylisoxazole-3-carboxamide;
(R)-5-(3-Fluoro-4-(trifluoromethyl)phenyl)-N-(1-hydroxybutan-2-yl)-4-methylisoxazole-3-carboxamide;
5-(4-Chloro-2-ethoxyphenyl)-N-((1R,3S)-3-hydroxycyclohexyl)-4-methyl-isoxazole-3-carboxamide;
Racemic-5-(4-Chloro-2-ethoxyphenyl)-N-(cis-2-hydroxycyclohexyl)-4-methylisoxazole-3-carboxamide;
(R)-4-Chloro-N-(tetrahydrofuran-3-yl)-5-(4-(trifluoromethyl)phenyl)isoxazole-3-carboxamide;
4-Chloro-N-((1R,2S)-2-hydroxycyclopentyl)-5-(4-(trifluoromethyl)phenyl)-isoxazole-3-carboxamide;
(R)-4-Chloro-5-(3-fluoro-4-(trifluoromethyl)phenyl)-N-(tetrahydrofuran-3-yl)isoxazole-3-carboxamide;
4-Chloro-5-(3-fluoro-4-(trifluoromethyl)phenyl)-N-((1R, 2S)-2-hydroxycyclopentyl)isoxazole-3-carboxamide;
N-Cyclopentyl-5-(3-fluoro-4-(trifluoromethyl)phenyl)-4-methylisoxazole-3-carboxamide;
5-(4-Chloro-2-ethoxyphenyl)-4-methyl-N—((S)-1,1,1-trifluoropropan-2-yl)isoxazole-3-carboxamide;
5-(4-Chloro-2-ethoxyphenyl)-N-(3,3-difluorocyclobutyl)-4-methylisoxazole-3-carboxamide;
(S)-5-(3-Fluoro-4-(trifluoromethyl)phenyl)-4-methyl-N-(3-methylbutan-2-yl)isoxazole-3-carboxamide;
4-Chloro-N-isopropyl-5-(4-(trifluoromethyl)phenyl)isoxazole-3-carboxamide;
N-(3,3-Difluorocyclobutyl)-5-(3-fluoro-4-(trifluoromethyl)phenyl)-4-methylisoxazole-3-carboxamide;
(R)-5-(3-Fluoro-4-(trifluoromethyl)phenyl)-N-(1-hydroxy-3-methylbutan-2-yl)-4-methylisoxazole-3-carboxamide;
4-Chloro-5-(4-chlorophenyl)-N-(cyclopropylmethyl)isoxazole-3-carboxamide;
4-Bromo-5-[4-(trifluoromethyl)phenyl]-N-(cyclopropylmethyl)isoxazole-3-carboxamide; or a pharmaceutically acceptable salt thereof.

The isoxazole-3-carboxamide derivatives of the invention may be prepared by methods known in the art of organic chemistry in general.

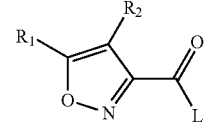

Formula II

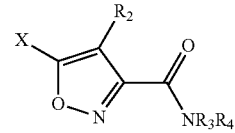

Formula III

Formula IV

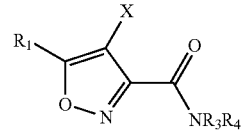

Formula V

Formula VI

Isoxazole-3-carboxamide derivatives of Formula I may for instance be prepared from compounds of Formula II wherein L is a leaving group, such as a halogen or an acyloxy group, and wherein $R_1$ and $R_2$ have the meaning as previously defined, by nucleophilic displacement of the leaving group with an amine of formula $NHR_3R_4$. Compounds of Formula II where L is an acyloxy group may be prepared from compounds of Formula II where L is hydroxy, by reaction with for example chloroformate in the presence of a base such as N-methylmorpholine.

Isoxazole-3-carboxamide derivatives of Formula I may be prepared from compounds of Formula II wherein L is hydroxy, by reaction with, for example, oxalyl chloride with or without the presence of a catalyst such as N,N-dimethylformamide and further treatment with the appropriate amine $NHR_3R_4$ (J. Am. Chem. Soc., Vol. 108, No. 22, 6950-6960, 1986).

Isoxazole-3-carboxamide derivatives of Formula I may be prepared from compounds of Formula II where L is hydroxy, by treatment with one or more standard (peptide) coupling reagents well known in the art, such as O-(7-azabenzotriazol-1-yl)-N,N,N',N'-tetramethyluronium hexafluorophosphate (HATU), dicyclohexylcarbodiimide (DCC), diisopropylcarbodiimide (DIC), or (benzotriazol-1-yl-oxy-trispyrrolidino-phosphonium-hexafluorophosphate (PYBOP) and further treatment with the appropriate amine $NHR_3R_4$ (J. Am. Chem. Soc., Vol. 108, No. 22, 6950-6960, 1986).

Isoxazole-3-carboxamide derivatives of Formula I may be prepared from compounds of Formula II where L is acyloxy, by treatment with the appropriate amine $NHR_3R_4$, in an appropriate solvent, at temperatures between 50 to 200° C.

using either conventional or microwave heating and a reaction time between 5 minutes and 30 hours.

In the alternative, compounds of Formula I may be prepared from compounds of Formula III where X is halogen by treatment with compounds of Formula IV, wherein $R_1$ is as previously defined and wherein $M_2$ is a boronic acid or a boronic acid ester, using a Suzuki reaction (Chem. Rev. 95, 2457-2483, 1995) or a modification thereof.

Similarly, isoxazole-3-carboxamide derivatives of Formula I may be prepared from compounds of Formula V by treatment with compounds of Formula VI, where $M_2$ is a boronic acid or a boronic acid ester, using a Suzuki reaction (Chem. Rev. 95, 2457-2483, 1995) or a modification thereof.

Compounds of Formula IV and Formula VI which serve as starting materials are commercially available or may be prepared by a variety of methods known in the art.

described in the general reference Davies, D. T. *Aromatic Heterocyclic Chemistry* (Oxford University Press: Oxford 1995).

Compounds of Formula X and Formula XI, wherein $R_7$ is $CO_2Et$, which serve as starting materials are commercially available or may be prepared by a variety of methods known in the art. Compounds of Formula III, where X is halogen may be prepared from compounds of Formula VIII, by treatment with the appropriate amine $NHR_3R_4$, in an appropriate solvent, at temperatures between 50 to 200° C. using either conventional or microwave heating and the reaction time between 5 minutes and 30 hours.

Compounds of Formula V, where X is halogen may be prepared from compounds of Formula IX, by treatment with the appropriate amine $NHR_3R_4$, in an appropriate solvent, at temperatures between 50 to 200° C. using either conventional or microwave heating and the reaction time between 5 minutes and 30 hours.

Formula VII
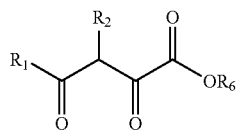

Formula VIII
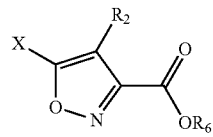

Formula IX
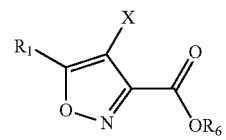

Formula X
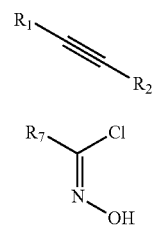

Formula XI

Formula XII

Formula XIII
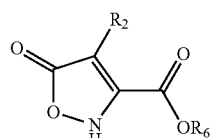

Formula XIV
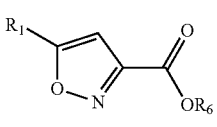

Formula XV
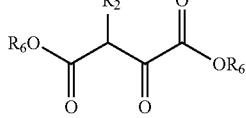

Compounds of Formula II, where L is alkoxy, may be prepared from compounds of Formula VII, wherein $R_1$ and $R_2$ have the previously given meaning, and wherein $R_6$ is ($C_{1-4}$) alkyl, by treatment with hydroxylamine in a suitable solvent.

Compounds of Formula II, where L is alkoxy, may be prepared from compounds of Formula VIII wherein $R_2$ and $R_6$ have the previously given meaning, and wherein X is halogen, by treatment with compounds of Formula IV, where $M_2$ is a boronic acid or a boronic acid ester, using a Suzuki reaction (Chem. Rev. 95, 2457-2483, 1995) or a modification thereof.

Compounds of Formula II, where L is alkoxy, may be prepared from compounds of Formula IX wherein $R_1$ and $R_6$ have the previously given meaning, and wherein X is halogen, by treatment with compounds of Formula VI, where $M_2$ is a boronic acid or a boronic acid ester, using a Suzuki reaction (Chem. Rev. 95, 2457-2483, 1995) or a modification thereof.

Furthermore, compounds of Formula II where L is alkoxy, may be prepared by reaction of compounds of Formula X, wherein $R_1$ and $R_2$ have the previously given meaning, in the presence of compounds of Formula XI in a suitable solvent as Compounds of Formula VII may be prepared from compounds of Formula XII by condensation with diethyl oxalate in the presence of a suitable base such as sodium ethoxide. Compounds of Formula XII which serve as starting materials are commercially available or may be prepared by a variety of methods known in the art.

Compounds of Formula VIII may be prepared from compounds of Formula XIII by treatment with but not restricted to, for example, phoshporusoxy bromide in the presence of a suitable base such as triethylamine.

Compounds of Formula IX, where $R_2$ is halogen may be prepared from compounds of Formula XIV, using methods well known in the art for halogenating heterocyclic rings. Such as methods described in the general reference Davies, D. T. *Aromatic Heterocyclic Chemistry* (Oxford University Press: Oxford 1995).

Compounds of Formula XIII may be prepared from compounds of Formula XV by treatment with hydroxylamine in a suitable solvent.

Compounds of Formula XIV may be prepared from compounds of Formula XVIII by treatment with hydroxylamine in a suitable solvent.

Furthermore, compounds of Formula XIV may be prepared by reaction of compounds of Formula XVI in the presence of compounds of Formula XI in a suitable solvent as described in the general reference Davies, D. T. (supra). Compounds of Formula XVI which serve as starting materials are commercially available or may be prepared by a variety of methods known in the art.

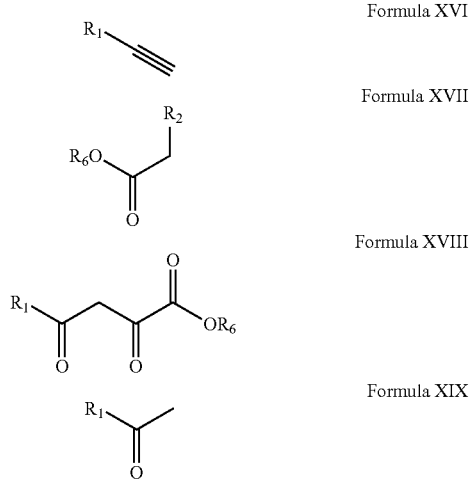

Formula XVI

Formula XVII

Formula XVIII

Formula XIX

Compounds of Formula XV may be obtained from commercial sources, prepared from compounds of Formula XVII using literature procedures or modifications of literature procedures known to those persons skilled in the art. For example, compounds of Formula XV where $R_1$ is ethyl and $R_2$ is methyl may be prepared by condensation of diethyl oxalate and ethyl propionate in the presence of a suitable base such as sodium ethoxide in a solvent such as ethanol.

Compounds of Formula XVIII, may be prepared from compounds of Formula XIX by condensation with diethyl oxalate in the presence of a suitable base such as sodium ethoxide. Compounds of Formula XIX which serve as starting materials are commercially available or may be prepared by a variety of methods known in the art.

The skilled person will likewise appreciate that various isoxazole-3-carboxamide derivatives of Formula I may be obtained by appropriate conversion reactions of functional groups corresponding to certain of the substituents $R_3$-$R_4$. For example, compounds of Formula I wherein $R_3$ or $R_4$ is an optionally substituted alkyl or cycloalkyl group, may be prepared by the reaction of a compound of Formula I wherein $R_3$ or $R_4$ is hydrogen with an appropriately functionalised alkyl or cycloalkyl halide, in the presence of a base such as potassium carbonate.

The isoxazole-3-carboxamide derivatives of Formula I and their salts may contain at least one centre of chirality, and exist therefore as stereoisomers, including enantiomers and diastereomers. The present invention includes the aforementioned stereoisomers within its scope and each of the individual R and S enantiomers of the compounds of Formula I and their salts, substantially free, i.e. associated with less than 5%, preferably less than 2%, in particular less than 1% of the other enantiomer, and mixtures of such enantiomers in any proportions including the racemic mixtures containing substantially equal amounts of the two enantiomers.

Methods for asymmetric synthesis or chiral separation whereby the pure stereoisomers are obtained are well known in the art, e.g. synthesis with chiral induction or starting from commercially available chiral substrates, or separation of stereoisomers, for example using chromatography on chiral media or by crystallisation with a chiral counter-ion.

Pharmaceutically acceptable salts may be obtained by treating a free base of a compound of Formula I with a mineral acid such as hydrochloric acid, hydrobromic acid, phosphoric acid and sulfuric acid, or an organic acid such as for example ascorbic acid, citric acid, tartaric acid, lactic acid, maleic acid, malonic acid, fumaric acid, glycolic acid, succinic acid, propionic acid, acetic acid and methane sulfonic acid.

The compounds of the invention may exist in unsolvated as well as in solvated forms with pharmaceutically acceptable solvents such as water, ethanol and the like. In general, the solvated forms are considered equivalent to the unsolvated forms for the purpose of the invention.

The present invention further provides pharmaceutical compositions comprising an isoxazole-3-carboxamide derivative of the invention, including N,N-dimethyl-4-bromo-5-phenylisoxazole-3-carboxamide and N,N-diethyl-4-cyano-5-phenylisoxazole-3-carboxamide, or a pharmaceutically acceptable salt thereof, in admixture with pharmaceutically acceptable auxiliaries, and optionally other therapeutic agents. The term "acceptable" means being compatible with the other ingredients of the composition and not deleterious to the recipients thereof. Compositions include e.g. those suitable for oral, sublingual, subcutaneous, intravenous, epidural, intrathecal, intramuscular, transdermal, pulmonary, local, or rectal administration, and the like, all in unit dosage forms for administration. A preferred route of administration is the oral route.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., *Remington: The Science and Practice of Pharmacy* (20th Edition, Lippincott Williams & Wilkins, 2000, see especially Part 5: Pharmaceutical Manufacturing), the active agent may be compressed into solid dosage units, such as pills, tablets, or be processed into capsules, suppositories or patches. By means of pharmaceutically acceptable liquids the active agent may be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds may be used. Suitable carriers with which the active agent of the invention may be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The isoxazole-3-carboxamide derivatives of the invention were found to have modulatory properties at the vanilloid receptor (TRPV1 or VR1) as measured by a fluorescence based calcium flux assay using a Chinese Hamster Ovary cell line in which a human recombinant VR1 receptor had been stably expressed. Methods to construct such recombinant cell lines are well known in the art (Sambrook et al., Molecular Cloning: a Laboratory Manual, Cold Spring Harbor Laboratory Press, Cold Spring Harbor, 2000). The compounds of the invention are thus useful in the treatment of TRPV1 mediated disorders, such as in the treatment of acute and chronic pain disorders, acute and chronic neuropathic pain, acute and chronic inflammatory pain, respiratory diseases and in lower urinary tract disorders.

The compounds of the invention may be administered to humans in a sufficient amount and for a sufficient amount of time to alleviate the symptoms. Illustratively, dosage levels for humans may be in the range of 0.001-50 mg per kg body weight, preferably in a dosage of 0.01-20 mg per kg body weight.

The invention is illustrated by the following examples:
General Methods

Flash column chromatography was performed on silica gel. Semi-preparative high pressure liquid chromatography (semi-prep. HPLC) was performed using the method outlined below:

SunFire (C 18, OBD 5 µm) 19 mm×100 mm; 10-100% acetonitrile-water over a 9 minute gradient followed by 100% acetonitrile for 1 minute; 20 mL/min; 0.1% trifluoroacetic acid buffer; detection by UV at 215 nm.

1H NMR coupling constants are given in Hz.

Example 1

4-Chloro-5-(4-chlorophenyl)-N-(tetrahydro-2H-pyran-4-yl)isoxazole-3-carboxamide

A: Ethyl 444-chlorophenyl)-2,4-dioxobutanoate

To a solution of sodium ethoxide (4.4 g, 64.6 mmol) in absolute ethanol (60 mL) was added 4-chloroacetophenone (5.0 g, 32.3 mmol) and the reaction mixture was stirred for five minutes at room temperature. Diethyl oxalate (7.0 mL, 51.7 mmol) in absolute ethanol (10 mL) was added and the reaction mixture was heated to reflux for 4 hours. After cooling to room temperature, acetic acid (7.0 mL) was added and the resulting light yellow solid was filtered, washed with ethanol and dried in vacuo to obtain ethyl 4-(4-chlorophenyl)-2,4-dioxobutanoate (8.3 g, 32.6 mmol).

B: 5-(4-Chlorophenyl)isoxazole-3-carboxylate

Hydroxylamine hydrochloride (0.65 g, 9.42 mmol) was added to a suspension of ethyl 4-(4-chlorophenyl)-2,4-dioxobutanoate (2.0 g, 7.85 mmol) in absolute ethanol (40 mL) and the reaction was heated to reflux for 4 hours. After cooling to room temperature, the resulting white solid was filtered, washed with water and cold ethanol and dried in vacuo to obtain ethyl 5-(4-chlorophenyl)isoxazole-3-carboxylate (1.19 g, 4.73 mmol).

C: Ethyl 4-chloro-5-(4-chlorophenyl)isoxazole-3-carboxylate

A mixture of ethyl 5-(4-chlorophenyl)isoxazole-3-carboxylate (250 mg, 1.0 mmol) and N-chlorosuccinimide (267 mg, 2.0 mmol) in acetic acid (5 mL) was heated to reflux for 3 days. The reaction mixture was then allowed to cool to room temperature, poured over ice and the resulting pale yellow solid was collected, washed with portions of water, and dried to obtain ethyl 4-chloro-5-(4-chlorophenyl)isoxazole-3-carboxylate (234 mg, 0.82 mmol).

D: 4-Chloro-5-(4-chlorophenyl)-N-(tetrahydro-2H-pyran-4-yl)isoxazole-3-carboxamide A mixture of ethyl 4-chloro-5-(4-chlorophenyl)isoxazole-3-carboxylate (20 mg, 0.07 mmol) and 4-aminotetrahydropyran (83 µL, 0.7 mmol) in absolute ethanol (1 mL) was heated to reflux for 36 hours. The volatiles were removed in vacuo and the resulting residue was purified by silica gel chromatography, eluting with dichloromethane, to afford the title compound: (16.8 mg, 0.05 mmol).

MS (ESI) m/z (M+H$^+$): 341.1.

The method of Example 1 was further used to prepare the following compounds using alternative amines instead of 4-aminotetrahydropyran.

Example 2 (A)

4-Chloro-5-(4-chlorophenyl)-N-cyclopentylisoxazole-3-carboxamide

MS (ESI) m/z (M+H$^+$): 341.1.

Example 2 (B)

4-Chloro-N-((1R,4R)-4-methylcyclohexyl)-5-(4-(trifluoromethyl)phenyl)isoxazole-3-carboxamide A: Ethyl-4-chloro-5-(4-(trifluoromethyl)phenyl)isoxazole-3-carboxylate The title compound was prepared according to Example 12; Step A-C.

B: 4-Chloro-N-((1R,4R)-4-methylcyclohexyl)-5-(4-(trifluoromethyl)phenyl)isoxazole-3-carboxamide Using ethyl-4-chloro-5-(4-(trifluoromethyl)phenyl)isoxazole-3-carboxylate, in place of ethyl 4-chloro-5-(4-chlorophenyl)isoxazole-3-carboxylate gave the title compound.

MS (ESI) m/z (M+H$^+$): 387.0/389.0.

The following compounds were prepared according to Example 2 (B):

Example 2 (C)

4-Chloro-N-(tetrahydro-2H-pyran-4-yl)-5-(4-(trifluoromethyl)phenyl)isoxazole-3-carboxamide MS (ESI) m/z (M+H$^+$): 375.2/377.2.

Example 2 (D)

4-Chloro-N-((1S,2R)-2-(hydroxymethyl)cyclohexyl)-5-(4-(trifluoromethyl)phenyl) isoxazole-3-carboxamide MS (ESI) m/z (M+H$^+$): 403.0/405.0.

Example 2 (E)

4-Chloro-N-(2-((1R,3R)-3-hydroxycyclopentyl)ethyl)-5-(4-(trifluoromethyl)phenyl) isoxazole-3-carboxamide MS (ESI) m/z (M+H$^+$): 402.8/404.9.

Example 2 (F)

4-Chloro-N-((1R,4R)-4-hydroxycyclohexyl)-5-(4-(trifluoromethyl)phenyl)isoxazole-3-carboxamide MS (ESI) m/z (M+H$^+$): 389.0/390.0.

Example 2 (G)

4-Chloro-N-((1R,2R)-2-(hydroxymethyl)cyclohexyl)-5-(4-(trifluoromethyl)phenyl) isoxazole-3-carboxamide MS (ESI) m/z (M+H$^+$): 403.0/404.0.

Example 2 (H)

4-Chloro-N-cyclopentyl-5-(4-(trifluoromethyl)phenyl)isoxazole-3-carboxamide

MS (ESI) m/z (M+H$^+$): 359.0/360.0.

Example 2 (I)

4-Chloro-N-cyclobutyl-5-(4-(trifluoromethyl)phenyl)isoxazole-3-carboxamide

MS (ESI) m/z (M+H$^+$): 345.1/347.1.

Example 2 (J)

5-(4-Chlorophenyl)-N-cyclopentyl-4-methylisoxazole-3-carboxamide

A: Ethyl 5-(4-chlorophenyl)-4-methylisoxazole-3-carboxylate

The title compound was prepared according to Example 9; Step A-B.

B: 5-(4-Chlorophenyl)-N-cyclopentyl-4-methylisoxazole-3-carboxamide

Using ethyl 5-(4-chlorophenyl)-4-methylisoxazole-3-carboxylate, in place of ethyl 4-chloro-5-(4-(trifluoromethyl)phenyl)isoxazole-3-carboxylate gave the title compound.
MS (ESI) m/z (M+H$^+$): 305.2/307.2.

Example 2 (K)

5-(4-Chlorophenyl)-4-methyl-N-(tetrahydro-2H-pyran-4-yl)isoxazole-3-carboxamide

The title compound was prepared according to Example 2 (J).
MS (ESI) m/z (M+H$^+$): 321.2.

Example 2 (L)

N-Cyclopentyl-4-methyl-5-(4-(trifluoromethyl)phenyl)isoxazole-3-carboxamide

A: Ethyl 5-(4-(trifluoromethyl)phenyl)-4-methyl-isoxazole-3-carboxylate

The title compound was prepared according to Example 9; Step A-B, whereby 4-(trifluoromethyl)propiophenone was used instead of 4-chloropropiophenone.

B: N-Cyclopentyl-4-methyl-5-(4-(trifluoromethyl)phenyl)isoxazole-3-carboxamide

Using ethyl 5-(4-(trifluoromethyl)phenyl)-4-methylisoxazole-3-carboxylate, in place of ethyl 4-chloro-5-(4-(trifluoromethyl)phenyl)isoxazole-3-carboxylate gave the title compound.
MS (ESI) m/z (M+H$^+$): 339.0.

Example 2 (M)

N-(3-Hydroxycyclohexyl)-4-methyl-5-(4-(trifluoromethyl)phenyl)isoxazole-3-carboxamide (mix)

The title compound was prepared according to Example 2 (L).
MS (ESI) m/z (M+H$^+$): 369.0.

Example 2 (N)

4-Methyl-N-(tetrahydro-2H-pyran-4-yl)-5-(4-(trifluoromethyl)phenyl)isoxazole-3-carboxamide The title compound was prepared according to Example 2 (L).
MS (ESI) m/z (M+H$^+$): 355.0.

Example 2 (O)

4-Bromo-5-(4-bromophenyl)-N-cyclopentylisoxazole-3-carboxamide

A: Ethyl-5-(4-bromophenyl)isoxazole-3-carboxylate

The title compound was prepared according to Example 1; Steps A-B, whereby 4-bromoacetophenone was used instead of 4-chloroacetophenone.

B: Ethyl-4-bromo-5-(4-bromophenyl)isoxazole-3-carboxylate

The title compound was prepared according to Example 7; Step A.

C: 4-Bromo-5-(4-bromophenyl)-N-cyclopentylisoxazole-3-carboxamide

Using ethyl-4-bromo-5-(4-bromophenyl)isoxazole-3-carboxylate, in place of ethyl 4-chloro-5-(4-(trifluoromethyl)phenyl)isoxazole-3-carboxylate gave the title compound.
MS (ESI) m/z (M+H$^+$): 412.9.

Example 2 (P)

4-Chloro-5-(4-chlorophenyl)-N-(pentan-2-yl)isoxazole-3-carboxamide

The title compound was prepared according to Example 1. MS (ESI) m/z (M+H$^+$): 327.1.

Example 2 (O)

4-Chloro-5-(4-chlorophenyl)-N-cyclohexylisoxazole-3-carboxamide

The title compound was prepared according to Example 1. MS (ESI) m/z (M+H$^+$): 339.

Example 2 (R)

4-Chloro-5-(4-chlorophenyl)-N-cyclobutylisoxazole-3-carboxamide

The title compound was prepared according to Example 1. MS (ESI) m/z (M+H$^+$): 311.1.

Example 2 (S)

4-Chloro-5-(4-chlorophenyl)-N-(cyclopropylmethyl)isoxazole-3-carboxamide

The title compound was prepared according to Example 1. MS (ESI) m/z (M+H$^+$): 313.0.

Example 2 (T)

4-Bromo-5-[4-(trifluoromethyl)phenyl]-N-(cyclopropylmethyl)isoxazole-3-carboxamide A: Ethyl-4-bromo-5-(4-fluorophenyl)isoxazole-3-carboxylate The title compound was prepared according to Example 10 (M); Step A.

B: 4-Bromo-5-[4-(trifluoromethyl)phenyl]-N-(cyclopropylmethyl)isoxazole-3-carboxamide The title compound was prepared according to Example 1. MS (ESI) m/z (M+H$^+$): 391.0.

Example 3

(S)-4-Chloro-5-(4-chlorophenyl)-N-(tetrahydrofuran-3-yl)isoxazole-3-carboxamide

A: 4-Chloro-5-(4-chlorophenyl)isoxazole-3-carboxylic acid

To a solution of ethyl 4-chloro-5-(4-chlorophenyl)isoxazole-3-carboxylate (20 mg, 0.07 mmol) in methanol (0.5 mL), an aqueous solution of 1N NaOH (140 μL, 0.14 mmol) was added. The mixture was left to stand at room temperature for 2 hours, the reaction mixture was acidified using a 1N HCl solution and methanol was removed in vacuo. The aqueous mixture was extracted with ethylacetate (3×3 mL), the organics combined, dried with MgSO$_4$ and filtered before evaporation to dryness in vacuo to obtain 4-chloro-5-(4-chlorophenyl)isoxazole-3-carboxylic acid (18 mg, 0.07 mmol).

B: 4-Chloro-5-(4-chlorophenyl)isoxazole-3-carbonyl chloride

To a suspension of 4-chloro-5-(4-chlorophenyl)isoxazole-3-carboxylic acid (0.66 g, 2.58 mmol) and oxalyl chloride (0.9 mL, 10.32 mmol) in dichloromethane (30 mL) was added 2 drops of N,N-dimethylformamide. After the mixture was stirred 16 hours at room temperature, the volatiles were removed in vacuo to obtain 4-chloro-5-(4-chlorophenyl)isoxazole-3-carbonyl chloride (0.71 g, 2.53 mmol).

C: (S)-4-Chloro-5-(4-chlorophenyl)-N-(tetrahydrofuran-3-yl)isoxazole-3-carboxamide A mixture of 4-chloro-5-(4-chlorophenyl)isoxazole-3-carbonyl chloride (24 mg, 0.087 mmol), (S)-tetrahydrofuran-3-amine (13 μL, 0.13 mmol), and potassium carbonate (36 mg, 0.261 mmol) in dichloromethane (1 mL) was stirred for 48 hours. The volatiles were removed in vacuo, and the residue was purified by silica gel chromatography, eluting with dichloromethane 5% methanol in dichloromethane to afford the title compound: (19.1 mg, 0.059 mmol). MS (ESI) m/z (M+H$^+$): 327.2/329.2.

Example 4

4-Chloro-5-(4-chlorophenyl)-N-((1R,3S)-3-hydroxycyclohexyl)isoxazole-3-carboxamide To 18 mg (0.07 mmol) of 4-chloro-5-(4-chlorophenyl)isoxazole-3-carboxylic acid in anhydrous N,N-dimethylformamide (1 mL) was added O-(7-azabenzotriazol-1-yl)-N,N,N',N'-tetramethyluronium hexafluorophosphate (HATU; 27 mg, 0.07 mmol), followed by (1S,3R)-3-aminocyclohexanol (8.1 mg, 0.07 mmol) with stirring at room temperature. After 18 h, the solvent was removed in vacuo, and the residue was partitioned between water and ethyl acetate. The aqueous layer was separated and repeatedly extracted with ethyl acetate, the combined organic extracts were dried (MgSO$_4$), the solvent removed in vacuo and the residue was purified by preparative HPLC to afford the title compound: (5.3 mg, 0.015 mmol). MS (ESI) m/z (M+H$^+$): 354.9/356.9.

The method of Example 4 was further used to prepare the following compound using alternative amines instead of (1S,3R)-3-aminocyclohexanol.

Example 5 (A)

4-Chloro-N-(((1S,2R)-2-hydroxycyclohexyl)methyl)-5-(4-(trifluoromethyl)phenyl) isoxazole-3-carboxamide A: 4-Chloro-5-(4-(trifluoromethyl)phenyl)isoxazole-3-carboxylic acid The title compound was prepared according to Example 12; Steps A-D.

B: 4-Chloro-N-(((1S,2R)-2-hydroxycyclohexyl)methyl)-5-(4-(trifluoromethyl)phenyl) isoxazole-3-carboxamide Using 4-chloro-5-(4-(trifluoromethyl)phenyl)isoxazole-3-carboxylic acid, in place of 4-chloro-5-(4-chlorophenyl)isoxazole-3-carboxylic acid gave the title compound.
MS (ESI) m/z (M+H$^+$): 402.9/404.9.

Example 5 (B)

4-Chloro-N-(tetrahydro-2H-pyran-3-yl)-5-(4-(trifluoromethyl)phenyl)isoxazole-3-carboxamide The title compound was prepared according to Example 5 (A).
MS (ESI) m/z (M+H$^+$): 375.1/377.1.

Example 5 (C)

4-Chloro-5-(3,4-difluorophenyl)-N-(cis-2-(hydroxymethyl)cyclopentyl)isoxazole-3-carboxamide A: 4-Chloro-5-(3,4-difluorophenyl)isoxazole-3-carboxylic acid The title compound was prepared according to Example 6; Steps A-B.

B: 4-Chloro-5-(3,4-difluorophenyl)-N-(cis-2-(hydroxymethyl)cyclopentyl)isoxazole-3-carboxamide The title compound was prepared according to Example 5 (A).
MS (ESI) m/z (M+H$^+$): 357.3/359.3.

Example 5 (D)

4-Chloro-5-(4-chloro-3-fluorophenyl)-N-((1R,3S)-3-hydroxycyclopentyl)isoxazole-3-carboxamide A: Ethyl-4-chloro-5-(4-chloro-3-fluorophenyl)isoxazole-3-carboxylate The title compound was prepared according to Example 1; Steps A-C, whereby in Step A, 4-chloro-3-fluoroacetophenone was used instead of 4-chloroacetophenone.

B: 4-Chloro-5-(4-chloro-3-fluorophenyl)isoxazole-3-carboxylic acid

The title compound was prepared using the procedure of Example 3; Step A whereby LiOH was used instead of NaOH.

C: 4-Chloro-5-(4-chloro-3-fluorophenyl)-N-((1R,3S)-3-hydroxycyclopentyl)isoxazole-3-carboxamide The title compound was prepared according to Example 5 (A).
MS (ESI) m/z (M+H$^+$): 359.3/361.3.

Example 5 (E)

4-Chloro-5-(4-chloro-3-fluorophenyl)-N-((1R,2S)-2-(hydroxymethyl)cyclohexyl) isoxazole-3-carboxamide The title compound was prepared according to Example 5 (D).
MS (ESI) m/z (M+H$^+$): 387.3/389.3.

Example 5 (F)

5-(4-Chlorophenyl)-4-fluoro-N-((1R,3S)-3-hydroxycyclohexyl)isoxazole-3-carboxamide A: Ethyl 5-(4-chlorophenyl)isoxazole-3-carboxylate The title compound was prepared according to Example 1; Steps A-B.

B: 5-(4-Chlorophenyl)-4-fluoroisoxazole-3-carboxylic acid

The title compound was prepared according to Example 14; Steps A-B, whereby ethyl 5-(4-chlorophenyl)isoxazole-3-carboxylate was used instead of ethyl-5-(4-(trifluoromethyl)phenyl)isoxazole-3-carboxylate.

C: 5-(4-Chlorophenyl)-4-fluoro-N-((1R,3S)-3-hydroxycyclohexyl)isoxazole-3-carboxamide The title compound was prepared according to Example 5 (A).
MS (ESI) m/z (M+H$^+$): 338.9.

Example 5 (G)

4-Chloro-5-(4-fluorophenyl)-N-((1R,3S)-3-hydroxycyclohexyl)isoxazole-3-carboxamide A: 4-Chloro-5-(4-fluorophenyl)isoxazole-3-carboxylic acid The title compound was prepared according to Example 10 (I); Steps A-C.

B: 4-Chloro-5-(4-fluorophenyl)-N-((1R,3S)-3-hydroxycyclohexyl)isoxazole-3-carboxamide The title compound was prepared according to Example 5 (A).
MS (ESI) m/z (M+H$^+$): 339.0.

Example 6

4-Chloro-5-(3,4-difluorophenyl)-N-((1R,3S)-3-hydroxycyclohexyl)isoxazole-3-carboxamide A: Ethyl 4-chloro-5-(3,4-difluorophenyl)isoxazole-3-carboxylate The title compound was prepared according to Example 1; Steps A-C whereby in Step A, 3,4-fluoroacetophenone was used instead of 4-chloroacetophenone.

B: 4-Chloro-5-(3,4-difluorophenyl)isoxazole-3-carboxylic acid

The title compound was prepared using the procedure of Example 3; Step A whereby LiOH was used instead of NaOH.

C: 4-Chloro-5-(3,4-difluorophenyl)isoxazole-3-carbonyl chloride

The title compound was prepared using the procedure of Example 3; Step B.

D: 4-Chloro-5-(3,4-difluorophenyl)-N-((1R,3S)-3-hydroxycyclohexyl)isoxazole-3-carboxamide A suspension of (1S,3R)-3-aminocyclohexanol (46 mg, 0.40 mmol), N,N-diisopropylethylamine (0.21 mL, 1.20 mmol) and dichloromethane (15 mL) under argon was treated with a dichloromethane (15 mL) solution of 4-chloro-5-(3,4-difluorophenyl)-isoxazole-3-carbonyl chloride (112 mg, 0.40 mmol) at room temperature. After stirring for 2 hours the volatiles were removed in vacuo, and the residue was purified initially by silica gel chromatography, eluting with dichloromethane to 4% methanol in dichloromethane followed by RP HPLC (H$_2$O/MeCN/MeOH 48/48/4 [vol./vol.]) to afford the title compound: (86 mg, 0.24 mmol).
LC/MS m/z (M+H$^+$): 357.0/359.0.

Example 7

4-Bromo-5-(4-chlorophenyl)-N-cyclopentylisoxazole-3-carboxamide

A: Ethyl 4-bromo-5-(4-chlorophenyl)isoxazole-3-carboxylate

A mixture of ethyl 5-(4-chlorophenyl)isoxazole-3-carboxylate (0.66 g, 2.62 mmol) and N-bromosuccinimide (0.93 g, 5.2 mmol) in acetic acid (12 mL) was heated to reflux for 24 hours. An additional portion of N-bromosuccinimide (0.5 g, 2.8 mmol) was added and the reaction refluxed another 16 h. The reaction mixture was allowed to cool to room temperature, poured over ice and the resulting white solid was collected and purified by silica gel chromatography, eluting with dichloromethane to obtain ethyl 4-bromo-5-(4-chlorophenyl)isoxazole-3-carboxylate (0.62 g, 1.88 mmol).

B: 4-Bromo-5-(4-chlorophenyl)-N-cyclopentylisoxazole-3-carboxamide

A mixture of ethyl 4-bromo-5-(4-chlorophenyl)isoxazole-3-carboxylate (213 mg, 0.70 mmol) and cyclopentylamine (0.70 mL, 7.0 mmol) in absolute ethanol (8 mL) was heated to reflux overnight. The volatiles were removed in vacuo and the compound was purified by silica gel chromatography eluting with 2% methanol with dichloromethane to afford the title compound: (0.21 g, 0.57 mmol). MS (ESI) m/z (M+H$^+$): 370.9/368.8.

Example 8

5-(4-Chlorophenyl)-N-cyclopentyl-4-cyclopropylisoxazole-3-carboxamide

A mixture of 4-bromo-5-(4-chlorophenyl)-N-cyclopentyl-isoxazole-3-carboxamide (40 mg, 0.11 mmol), cyclopropylboronic acid (22 mg, 0.26 mmol), and tricyclohexylphosphine (6 mg, 0.02 mmol) in toluene (1 mL) was degassed with Argon. 2M aqueous potassium phosphate (0.35 mL, 0.7 mmol) and palladium(II) acetate were added and the reaction heated to 100° C. for 3 hours. The volatiles were removed in vacuo and compound was purified by silica gel chromatography eluting with 2% methanol in dichloromethane to afford the title compound: (6.8 mg, 0.02 mmol). MS (ESI) m/z (M+H$^+$): 331.2

Example 9

(S)-5-(4-Chlorophenyl)-4-methyl-N-(tetrahydrofuran-3-yl)isoxazole-3-carboxamide

A: Lithium enolate of ethyl 4-(4-chlorophenyl)-3-methyl-2,4-dioxobutanoate

A 1.0 M solution of lithium bis(trimethylsilyl)amide in tetrahydrofuran (30 mL, 30 mmol) in anhydrous diethyl ether (120 mL) under argon was cooled to −78° C. in a dry ice/acetone bath. A solution of 4-chloropropiophenone (5.0 g, 29.7 mmol) in anhydrous ether (24 mL) was added dropwise and the mixture was stirred an additional 45 minutes at −78° C. Diethyl oxalate (4.6 mL, 33.9 mmol) was added in one portion; the reaction was warmed to room temperature, and stirred overnight. The light yellow precipitate that formed was collected, washed with ether and dried under vacuum to obtain the lithium enolate of ethyl 4-(4-chlorophenyl)-3-methyl-2,4-dioxobutanoate (2.75 g, 10.0 mmol).

B: Ethyl 5-(4-chlorophenyl)-4-methylisoxazole-3-carboxylate

The lithium enolate of ethyl 4-(4-chlorophenyl)-3-methyl-2,4-dioxobutanoate (1.5 g, 5.5 mmol) and hydroxylamine hydrochloride (0.46 g, 6.6 mmol) in absolute ethanol (30 mL) were heated to reflux for 17 hours, cooled to room temperature, then cooled to 0° C. for 3 hours. The resulting white crystals were collected and dried under vacuum to obtain ethyl 5-(4-chlorophenyl)-4-methylisoxazole-3-carboxylate (0.55 g, 0.20 mmol).

C: 5-(4-Chlorophenyl)-4-methylisoxazole-3-carboxylic acid

To a solution of ethyl 5-(4-chlorophenyl)-4-methylisoxazole-3-carboxylate (63 mg, 0.24 mmol) in tetrahydrofuran (1.5 mL) was added a solution of lithium hydroxide hydrate (10 mg, 0.24 mmol) in water (1.5 mL). After stirring for 20 minutes, the reaction mixture was acidified with 1M HCl and extracted with dichloromethane three times. The combined dichloromethane extracts were washed with brine, dried over magnesium sulfate, and evaporated to obtain 5-(4-chlorophenyl)-4-methylisoxazole-3-carboxylic acid (55 mg, 0.23 mmol).

D: (S)-5-(4-Chlorophenyl)-4-methyl-N-(tetrahydrofuran-3-yl)isoxazole-3-carboxamide (S)-Tetrahydrofuran-3-amine (13 μL, 0.13 mmol) was added to a mixture of 5-(4-chlorophenyl)-4-methylisoxazole-3-carboxylic acid (23 mg, 0.10 mmol), 1-hydroxybenzotriazole hydrate (16 mg, 0.12 mmol), N-(3-dimethylaminopropyl)-N'-ethylcarbodiimide hydrochloride (22 mg, 0.12 mmol) and triethylamine (16 μL, 0.12 mmol) in tetrahydrofuran (0.8 mL) and N,N-dimethylformamide (0.1 mL). After stirring overnight, the volatiles were removed in vacuo and the compound was purified by silica gel chromatography eluting with 2% methanol in dichloromethane to afford the title compound: (21.6 mg, 0.07 mmol). MS (ESI) m/z (M+H$^+$): 307.0.

The method of Example 9 was further used to prepare the following compounds using alternative amines instead of (S)-tetrahydrofuran-3-amine.

Example 10 (A)

5-(4-Chlorophenyl)-N-cyclopentyl-4-methylisoxazole-3-carboxamide

MS (ESI) m/z (M+H$^+$): 305.2/307.3.

Example 10 (B)

4-Chloro-N-((1R,2S)-2-hydroxy-2,3-dihydro-1H-inden-1-yl)-5-(4-(trifluoromethyl)phenyl)isoxazole-3-carboxamide Using 4-chloro-5-(4-(trifluoromethyl)phenyl)isoxazole-3-carboxylic acid, synthesised according to Example 12, in place of 5-(4-chlorophenyl)-4-methylisoxazole-3-carboxylic acid. MS (ESI) m/z (M+H$^+$): 423.2.

Example 10 (C)

4-Chloro-N-(3-hydroxypiperidin-1-yl)-5-(4-(trifluoromethyl)phenyl)isoxazole-3-carboxamide The title compound was prepared according to Example 10 (B).
MS (ESI) m/z (M+H$^+$): 390.3.

Example 10 (D)

4-Bromo-5-(4-chlorophenyl)-N-propylisoxazole-3-carboxamide

Using 4-bromo-5-(4-(chlorophenyl)isoxazole-3-carboxylic acid, synthesised according to Letourneau, J. J. et al, *Tetrahedron Lett.* 2007, 48, 1739-1743, in place of 544-chlorophenyl)-4-methylisoxazole-3-carboxylic acid.
MS (ESI) m/z (M+H$^+$): 343.0/344.9.

Example 10 (E)

4-Bromo-N-butyl-5-(4-chlorophenyl)isoxazole-3-carboxamide

The title compound was prepared according to Example 10 (D).
MS (ESI) m/z (M+H$^+$): 356.4/358.9.

Example 10 (F)

4-Bromo-5-(4-chlorophenyl)-N-cyclopentylisoxazole-3-carboxamide

The title compound was prepared according to Example 10 (D).
MS (ESI) m/z (M+H$^+$): 368.9/370.9.

Example 10 (G)

4-Bromo-5-(4-chlorophenyl)-N-(tetrahydro-2H-pyran-4-yl)isoxazole-3-carboxamide

The title compound was prepared according to Example 10 (D).

$^1$H-NMR (300 MHz, CDCl$_3$+5% CD$_3$OD) δ 7.95 (d, 2H), 7.50 (d, 2H), 4.15 (m, 1H), 3.97 (m, 2H), 3.50 (m, 2H), 1.95 (m, 2H), 1.62 (m, 2H).

Example 10 (H)

4-Chloro-5-(4-chlorophenyl)-N-((1R,3S)-3-hydroxycyclopentyl)isoxazole-3-carboxamide Using 4-chloro-5-(4-chlorophenyl)isoxazole-3-carboxylic acid, synthesised according to Example 1, in place of 5-(4-chlorophenyl)-4-methylisoxazole-3-carboxylic acid.
MS (ESI) m/z (M+H$^+$): 341.2.

Example 10 (I)

4-Chloro-5-(4-fluorophenyl)-N-(3-hydroxycyclohexyl)isoxazole-3-carboxamide

A: Ethyl 5-(4-fluorophenyl)isoxazole-3-carboxylate

The title compound was prepared according to Example 1; Steps A-B whereby in Step A, 4-fluoroacetophenone was used instead of 4-chloroacetophenone.

B: Ethyl 4-chloro-5-(4-fluorophenyl)isoxazole-3-carboxylate

The title compound was prepared according to Example 1; Steps C whereby in Step C, ethyl 5-(4-fluorophenyl)isoxazole-3-carboxylate was used instead of ethyl 5-(4-chlorophenyl)isoxazole-3-carboxylate.

C: 4-Chloro-5-(4-fluorophenyl)isoxazole-3-carboxylic acid

The title compound was prepared using the procedure of Example 3; Step A whereby LiOH was used instead of NaOH.

D: 4-Chloro-5-(4-fluorophenyl)-N-(3-hydroxycyclohexyl)isoxazole-3-carboxamide

Using 4-chloro-5-(4-fluorophenyl)isoxazole-3-carboxylic acid, in place of 544-chlorophenyl)-4-methylisoxazole-3-carboxylic acid gave the title compound.
MS (ESI) m/z (M+H$^+$): 339.3.

Example 10 (J)

4-Chloro-5-(4-fluorophenyl)-N-((1R,3S)-3-hydroxycyclopentyl)isoxazole-3-carboxamide The title compound was prepared according to Example 10 (I).
MS (ESI) m/z (M+H$^+$): 325.4/327.4.

Example 10 (K)

4-Bromo-5-(3,4-dichlorophenyl)-N-(tetrahydro-2H-pyran-4-yl)isoxazole-3-carboxamide A: Ethyl-5-(3,4-dichlorophenyl)isoxazole-3-carboxylate The title compound was prepared according to Example 1; Steps A-B whereby in Step A, 3,4-dichloroacetophenone was used instead of 4-chloroacetophenone.

B: Ethyl 4-bromo-5-(3,4-dichlorophenyl)isoxazole-3-carboxylate

The title compound was prepared using the procedure of Example 7; Step A whereby ethyl-5-(3,4-dichlorophenyl)isoxazole-3-carboxylate was used instead of ethyl-5-(4-chlorophenyl)isoxazole-3-carboxylate.

C: 4-Bromo-5-(3,4-dichlorophenyl)isoxazole-3-carboxylic acid

The title compound was prepared using the procedure of Example 3; Step A whereby LiOH was used instead of NaOH.

D: 4-Bromo-5-(3,4-dichlorophenyl)-N-(tetrahydro-2H-pyran-4-yl)isoxazole-3-carboxamide Using 4-bromo-5-(3,4-dichlorophenyl)isoxazole-3-carboxylic acid, in place of 5-(4-chlorophenyl)-4-methylisoxazole-3-carboxylic acid gave the title compound.
MS (ESI) m/z (M+H$^+$): 418.9/420.9/422.9.

Example 10 (L)

4-Bromo-N-cyclopentyl-5-(3,4-dichlorophenyl)isoxazole-3-carboxamide

The title compound was prepared according to Example 10 (K).
MS (ESI) m/z (M+H$^+$): 402.8/404.9/406.9.

Example 10 (M)

4-Bromo-N-cyclopentyl-5-(4-(trifluoromethyl)phenyl)isoxazole-3-carboxamide

A: Ethyl-4-bromo-5-(4-(trifluoromethyl)phenyl)isoxazole-3-carboxylate

The title compound was prepared according to Example 7; whereby ethyl-5-(4-(trifluoromethyl)phenyl)isoxazole-3-carboxylate, which was synthesised following Example 12

Steps A-B, was used instead of ethyl 5-(4-chlorophenyl)isoxazole-3-carboxylate.

B: 4-Bromo-5-(4-(trifluoromethyl)phenyl)isoxazole-3-carboxylic acid

The title compound was prepared using the procedure of Example 3; Step A whereby LiOH was used instead of NaOH.

C: 4-Bromo-N-cyclopentyl-5-(4-(trifluoromethyl)phenyl)isoxazole-3-carboxamide

Using 4-bromo-5-(4-(trifluoromethyl)phenyl)isoxazole-3-carboxylic acid, in place of 5-(4-chlorophenyl)-4-methylisoxazole-3-carboxylic acid gave the title compound.
MS (ESI) m/z (M+H$^+$): 403.0/405.0.

Example 10 (N)

4-Bromo-N-(tetrahydro-2H-pyran-4-yl)-5-(4-(trifluoromethyl)phenyl)isoxazole-3-carboxamide The title compound was prepared according to Example 10 (M). MS (ESI) m/z (M+H$^+$): 419.0/421.0.

Example 10 (O)

4-Bromo-N-(tetrahydro-2H-pyran-4-yl)-5-(4-(trifluoromethoxy)phenyl)isoxazole-3-carboxamide A: Ethyl-5-(4-(trifluoromethoxy)phenyl)isoxazole-3-carboxylate The title compound was prepared according to Example 1; Steps A-C whereby in Step A, 4-(trifluoromethoxy)acetophenone was used instead of 4-chloroacetophenone.

B: Ethyl-4-bromo-5-(4-(trifluoromethoxy)phenyl)isoxazole-3-carboxylate

The title compound was prepared according to Example 7; whereby ethyl-5-(4-(4-(trifluoromethoxy)phenyl)isoxazole-3-carboxylate was used instead of ethyl 5-(4-chlorophenyl)isoxazole-3-carboxylate.

C: 4-Bromo-5-(4-(trifluoromethoxy)phenyl)isoxazole-3-carboxylic acid

The title compound was prepared using the procedure of Example 3; Step A whereby LiOH was used instead of NaOH.

D: 4-Bromo-N-(tetrahydro-2H-pyran-4-yl)-5-(4-(trifluoromethoxy)phenyl)isoxazole-3-carboxamide Using 4-bromo-5-(4-(trifluoromethoxy)phenyl)isoxazole-3-carboxylic acid, in place of 5-(4-chlorophenyl)-4-methylisoxazole-3-carboxylic acid gave the title compound.
MS (ESI) m/z (M+H$^+$): 434.9/436.9.

Example 10 (P)

4-Bromo-N-cyclopentyl-5-(4-fluorophenyl)isoxazole-3-carboxamide

A: Ethyl-5-(4-fluorophenyl)isoxazole-3-carboxylate

The title compound was prepared according to Example 10 (I); Step A.

B: Ethyl-4-bromo-5-(4-fluorophenyl)isoxazole-3-carboxylate

The title compound was prepared according to Example 7; whereby ethyl-5-(4-fluorophenyl)isoxazole-3-carboxylate was used instead of ethyl 5-(4-chlorophenyl)isoxazole-3-carboxylate.

C:
4-Bromo-5-(4-fluorophenyl)isoxazole-3-carboxylic acid

The title compound was prepared using the procedure of Example 3; Step A whereby LiOH was used instead of NaOH.

D: 4-Bromo-N-cyclopentyl-5-(4-fluorophenyl)isoxazole-3-carboxamide

Using 4-bromo-5-(4-fluorophenyl)isoxazole-3-carboxylic acid, in place of 5-(4-chlorophenyl)-4-methylisoxazole-3-carboxylic acid gave the title compound.
MS (ESI) m/z (M+H$^+$): 353.0/355.0.

Example 11

4-Cyano-N-cyclopentyl-5-(4-(trifluoromethyl)phenyl)isoxazole-3-carboxamide

A: Ethyl 4-cyano-5-(4-(trifluoromethyl)phenyl)isoxazole-3-carboxylate

Triethylamine (0.98 mL, 7.0 mmol) was added to a −5° C. solution of 4-trifluoromethylbenzoylacetonitrile (1.5 g, 7.0 mmol) in ethanol (15 mL) and the mixture was stirred for 20 minutes. A solution of ethyl 2-chloro-2-(hydroxyimino)acetate (1.06 g, 7.0 mmol) in ethanol (5 mL) was added to the reaction over 15 minutes. After stirring at room temperature for 72 hours, the cream-colored solid which formed was collected by filtration, washed with cold water and dried in vacuo to obtain ethyl 4-cyano-5-(4-(trifluoromethyl)phenyl)isoxazole-3-carboxylate (1.84 g, 5.93 mmol).

B: 4-Cyano-N-cyclopentyl-5-(4-(trifluoromethyl)phenyl)isoxazole-3-carboxamide

A mixture of ethyl 4-cyano-5-(4-(trifluoromethyl)phenyl)isoxazole-3-carboxylate (150 mg, 0.48 mmol) and cyclopentylamine (0.24 mL, 2.4 mmol) in ethanol (5 mL) was heated to 82° C. for 16 hours. The volatiles were removed in vacuo and the residue was purified by silica gel chromatography, eluting with 5% methanol in dichloromethane to afford the title compound: (130 mg, 0.37 mmol). $^1$H NMR (300 MHz, CDCl$_3$) δ 8.27 (m, 2H), 7.86 (m, 2H), 6.68 (br. d, 1H), 4.43 (m, 1H), 2.11 (m, 2H), 1.85-1.45 (m, 6H).

Example 12

4-Chloro-5-(4-(trifluoromethyl)phenyl)-N-(3-hydroxyphenyl)isoxazole-3-carboxamide A: Ethyl 2,4-dioxo-4-(4-(trifluoromethyl)phenyl)butanoate Sodium ethoxide (35 mL, 191 mmol), a 21 wt. % solution in ethanol, was diluted with tetrahydrofuran (15 mL) and cooled to 0° C. A solution of 4-(trifluoromethyl)-acetophenone (4.5 g, 23.9 mmol) and diethyl oxalate (6.5 mL, 95.6 mmol) in tetrahydrofuran (20 mL) was added dropwise by addition funnel over 10 minutes. After stirring an additional 10 minutes at room temperature, the reaction mixture was diluted with diethyl ether, and 1M HCl (80 mL) was added. The layers were separated and the aqueous layer was extracted with two additional portions of diethyl ether. The combined ether extracts were washed with brine, dried over MgSO$_4$, and reduced in vacuo to obtain the title compound (6.89 g, 23.9 mmol).

B: Ethyl 5-(4-(trifluoromethyl)phenyl)isoxazole-3-carboxylate

A mixture of ethyl 2,4-dioxo-4-(4-(trifluoromethyl)phenyl)butanoate (6.89 g, 23.9 mmol) and hydroxylamine hydrochloride (2.0 g, 28.7 mmol) in ethanol (120 mL) was stirred at reflux overnight. The volatiles were removed in vacuo, and the residue purified by silica gel chromatography, eluting with dichloromethane to obtain the title compound (4.5 g, 15.6 mmol).

C: Ethyl 4-chloro-5-(4-(trifluoromethyl)phenyl)isoxazole-3-carboxylate

To a suspension of ethyl 5-(4-(trifluoromethyl)phenyl)isoxazole-3-carboxylate (3.3 g, 11.6 mmol) in acetic acid (60 mL) was added N-chlorosuccinimide (3.1 g, 23.2 mmol). Upon heating to 75° C., a homogenous solution formed. After heating for 16 hours a further portion of N-chlorosuccinimide (1.5 g, 11.2 mmol) was added and the reaction was heated at 75° C. for another 16 hours. After cooling to ambient temperature, the reaction mixture was poured over ice. The white crystals which formed were collected by vacuum filtration and purified by silica gel chromatography, eluting with dichloromethane to obtain the title compound (3.2 g, 10.0 mmol).

D: 4-Chloro-5-(4-(trifluoromethyl)phenyl)isoxazole-3-carboxylic acid

A solution of lithium hydroxide hydrate (126 mg, 3.0 mmol) in water (18 mL) was added to a solution of ethyl 4-chloro-5-(4-(trifluoromethyl)phenyl)isoxazole-3-carboxylate (0.96 g, 3.0 mmol) in tetrahydrofuran (15 mL). After stirring for 45 minutes, the reaction mixture was diluted with dichloromethane (30 mL), and the aqueous layer was adjusted to pH=2 with 6N aqueous HCl. The resulting mixture was extracted 3 times with dichloromethane, the dichloromethane layers were combined, dried over Na$_2$SO$_4$, and concentrated in vacuo to obtain the title compound (0.88 g, 3.0 mmol).

E: 4-Chloro-5-(4-(trifluoromethyl)phenyl)isoxazole-3-carbonyl chloride

To a mixture of 4-chloro-5-(4-(trifluoromethyl)phenyl)isoxazole-3-carboxylic acid (0.33 g, 1.13 mmol), oxalyl chloride (0.45 mL, 5.16 mmol) and dichloromethane (10 mL) was added a drop of N,N-dimethylformamide. The reaction mixture was stirred at room temperature for 6 hours. The volatiles were removed in vacuo to obtain 4-chloro-5-(4-(trifluoromethyl)phenyl)isoxazole-3-carbonyl chloride (0.34 g, 1.1 mmol)

F: 4-Chloro-5-(4-(trifluoromethyl)phenyl)-N-(3-hydroxyphenyl)isoxazole-3-carboxamide A mixture of 4-chloro-5-(4-(trifluoromethyl)phenyl)isoxazole-3-carbonyl chloride (15 mg, 0.05 mmol), 3-aminophenol (12.7 mg, 0.10 mmol) and potassium carbonate (7 mg, 0.05 mmol) in dichloromethane (8 mL) was heated to 45° C. overnight. The volatiles were removed in vacuo and the compound was purified by silica gel chromatography eluting with 3% methanol in dichloromethane to afford the title compound: (7.7 mg, 0.02 mmol). MS (ESI) m/z (M+H$^+$): 383.1.

The method of Example 12 was further used to prepare the following compounds using alternative amines instead of 3-aminophenol.

Example 13 (A)

4-Chloro-N-((1R,3S)-3-hydroxycyclopentyl)-5-(4-(trifluoromethyl)phenyl)isoxazole-3-carboxamide MS (ESI) m/z (M+H$^+$): 374.9/376.9.

Example 13 (B)

4-Chloro-N-((1R,3S)-3-hydroxycyclohexyl)-5-(4-(trifluoromethyl)phenyl)isoxazole-3-carboxamide MS (ESI) m/z (M+H$^+$): 388.9/391.0.

Example 13 (C)

4-Chloro-N-(5-hydroxypentyl)-5-(4-(trifluoromethyl)phenyl)isoxazole-3-carboxamide $^1$H-NMR (300 MHz, CD$_3$OD) δ 8.19 (d, 2H), 7.8 (d, 2H), 3.5 (m, 2H), 3.38 (m, 2H), 1.6 (m, 4H), 1.25 (m, 2H).

Example 13 (D)

4-Chloro-N-(2-(hydroxymethyl)phenyl)-5-(4-(trifluoromethyl)phenyl)isoxazole-3-carboxamide $^1$H-NMR (300 MHz, CD$_3$OD) δ 10.05 (d, 1H), 8.31 (d, 1H), 8.19 (d, 2H), 7.82 (d, 2H), 7.41 (dt, 1H), 7.25 (d, 1H), 7.16 (t, 1H), 4.85 (s, 2H).

Example 13 (E)

4-Chloro-N-((1R,3R,5S)-3,5-dihydroxycyclohexyl)-5-(4-(trifluoromethyl)phenyl) isoxazole-3-carboxamide MS (ESI) m/z (M+H$^+$): 405.4.

Example 13 (F)

4-Chloro-N-((1S,3R)-3-hydroxycyclopentyl)-5-(4-(trifluoromethyl)phenyl)isoxazole-3-carboxamide MS (ESI) m/z (M+H$^+$): 375.0/377.0.

Example 13 (G)

Racemic-4-Chloro-N-((trans-3-hydroxycyclohexyl)-5-(4-(trifluoromethyl)phenyl) isoxazole-3-carboxamide MS (ESI) m/z (M+H$^+$): 388.9.

Example 13 (H)

4-Chloro-N-((1S,2S,3R,4R)-3-(hydroxymethyl)bicyclo[2.2.1]hept-5-en-2-yl)-5-(4-(trifluoromethyl)phenyl)isoxazole-3-carboxamide MS (ESI) m/z (M+H$^+$): 412.9/414.9.

Example 13 (I)

4-Chloro-N-morpholino-5-(4-(trifluoromethyl)phenyl)isoxazole-3-carboxamide $^1$H-NMR (300 MHz, CD$_3$OD) δ 8.4 (d, 2H), 8.1 (d, 2H), 3.97 (m, 4H), 3.10 (m, 4H).

Example 13 (J)

4-Chloro-N-((1S,3R)-3-hydroxycyclohexyl)-5-(4-(trifluoromethyl)phenyl)isoxazole-3-carboxamide MS (ESI) m/z (M+H$^+$): 388.9.

Example 13 (K)

4-Chloro-N-(3-(hydroxymethyl)phenyl)-5-(4-(trifluoromethyl)phenyl)isoxazole-3-carboxamide MS (ESI) m/z (M+H$^+$): 396.8/398.8.

Example 13 (L)

4-Chloro-N-(3-hydroxypropyl)-5-(4-(trifluoromethyl)phenyl)isoxazole-3-carboxamide $^1$H-NMR (300 MHz, CD$_3$OD) δ 8.19 (d, 2H), 7.8 (d, 2H), 3.65 (m, 2H), 3.41 (m, 2H), 1.75 (m, 2H).

Example 13 (M)

4-Chloro-N-((tetrahydro-2H-pyran-3-yl)methyl)-5-(4-(trifluoromethyl)phenyl)isoxazole-3-carboxamide MS (ESI) m/z (M+H$^+$): 389.1/391.1.

Example 13 (N)

N-(3-Aminophenyl)-4-chloro-5-(4-(trifluoromethyl)phenyl)isoxazole-3-carboxamide

MS (ESI) m/z (M+H$^+$): 382.1/384.1.

Example 13 (O)

4-Chloro-N-(((1S,3S)-3-hydroxycyclopentyl)methyl)-5-(4-(trifluoromethyl)phenyl) isoxazole-3-carboxamide MS (ESI) m/z (M+H$^+$): 388.9/391.0.

Example 13 (P)

4-Chloro-N-cyclohexyl-5-(4-(trifluoromethyl)phenyl)isoxazole-3-carboxamide

MS (ESI) m/z (M+H$^+$): 373.0/375.0.

Example 13 (Q)

4-Chloro-N-((1S,2R,3S,4R)-3-(hydroxymethyl)bicyclo[2.2.1]heptan-2-yl)-5-(4-(trifluoromethyl)phenyl) isoxazole-3-carboxamide MS (ESI) m/z (M+H$^+$): 415.0/416.9.

Example 13 (R)

4-Chloro-N-((1S,6R)-6-(hydroxymethyl)cyclohex-3-enyl)-5-(4-(trifluoromethyl)phenyl)-isoxazole-3-carboxamide MS (ESI) m/z (M+H$^+$): 401.0/402.0.

Example 13 (S)

Racemic-4-Chloro-N-(cis-2-hydroxycyclohexyl)-5-(4-(trifluoromethyl)phenyl)isoxazole-3-carboxamide MS (ESI) m/z (M+H$^+$): 389.0/390.0.

Example 13 (T)

4-Chloro-N-(((1S,3R)-3-hydroxycyclopentyl)methyl)-5-(4-(trifluoromethyl)phenyl) isoxazole-3-carboxamide MS (ESI) m/z (M+H$^+$): 388.9/390.9.

Example 13 (U)

4-Chloro-N-(4-hydroxybutyl)-5-(4-(trifluoromethyl)phenyl)isoxazole-3-carboxamide $^1$H-NMR (300 MHz, CD$_3$OD) δ 8.19 (d, 2H), 7.8 (d, 2H), 3.5 (m, 2H), 3.39 (m, 2H), 1.6 (m, 4H).

Example 13 (V)

4-Chloro-N-((1S,2R,3S,4R)-3-(hydroxymethyl)bicyclo[2.2.1]hept-5-en-2-yl)-5-(4-(trifluoromethyl)phenyl)isoxazole-3-carboxamide MS (ESI) m/z (M+H$^+$): 413.0/415.0.

Example 13 (W)

Racemic-4-Chloro-N-((cis)-3-(hydroxymethyl)bicyclo[2.2.1]heptan-2-yl)-5-(4-(trifluoromethyl)phenyl)isoxazole-3-carboxamide MS (ESI) m/z (M+H$^+$): 415.0/416.0.

Example 13 (X)

4-Chloro-N-cyclohexyl-5-(4-fluorophenyl)isoxazole-3-carboxamide

A:
4-Chloro-5-(4-fluorophenyl)isoxazole-3-carboxylic acid

The title compound was prepared according to Example 10 (I); Steps A-C.

B: 4-Chloro-5-(4-fluorophenyl)isoxazole-3-carbonyl chloride

The title compound was prepared according to Example 12; Step E.

C: 4-Chloro-N-cyclohexyl-5-(4-fluorophenyl)isoxazole-3-carboxamide

Using 4-chloro-5-(4-fluorophenyl)isoxazole-3-carbonyl chloride, in place of 4-chloro-5-(4-(trifluoromethyl)phenyl) isoxazole-3-carbonyl chloride gave the title compound. MS (ESI) m/z (M+H$^+$): 323.3/325.3.

The following compounds were prepared according to Example 13 (X):

Example 13 (Y)

4-Chloro-N-cyclopentyl-5-(4-fluorophenyl)isoxazole-3-carboxamide

MS (ESI) m/z (M+H$^+$): 309.3/311.3.

Example 13 (Z)

4-Chloro-N-cyclobutyl-5-(4-fluorophenyl)isoxazole-3-carboxamide

MS (ESI) m/z (M+H$^+$): 295.3/297.4.

Example 13 (AA)

4-Chloro-5-(4-fluorophenyl)-N-((1R,2S)-2-(hydroxymethyl)cyclohexyl)isoxazole-3-carboxamide MS (ESI) m/z (M+H$^+$): 353.3/355.2.

Example 13 (AB)

4-Chloro-5-(4-fluorophenyl)-N-(tetrahydro-2H-pyran-4-yl)isoxazole-3-carboxamide

MS (ESI) m/z (M+H$^+$): 325.3.

Example 13 (AC)

4-Chloro-5-(4-fluorophenyl)-N-((1R,3S)-3-(hydroxymethyl)cyclopentyl)isoxazole-3-carboxamide MS (ESI) m/z (M+H$^+$): 339.2/341.2.

Example 13 (AD)

4-Chloro-5-(4-fluorophenyl)-N-(2,2,2-trifluoroethyl)isoxazole-3-carboxamide $^1$H-NMR (300 MHz, CDCl$_3$) δ 8.08 (m, 2H), 7.25 (m, 2H), 7.05 (bt, 1H), 4.13 (m, 2H).

Example 13 (AE)

4-Chloro-5-(4-chlorophenyl)-N-(3-methylcyclohexyl)isoxazole-3-carboxamide

A: Ethyl 4-Chloro-5-(4-chlorophenyl)isoxazole-3-carboxylate

The title compound was prepared according to Example 1; Steps A-C.

B:
4-Chloro-5-(4-chlorophenyl)isoxazole-3-carboxylic acid

The title compound was prepared using the procedure of Example 3; Step A whereby LiOH was used instead of NaOH.

C: 4-Chloro-5-(4-chlorophenyl)isoxazole-3-carbonyl chloride

The title compound was prepared according to Example 12; Steps E.

D: 4-Chloro-5-(4-chlorophenyl)-N-(3-methylcyclohexyl)isoxazole-3-carboxamide

Using 4-chloro-5-(4-chlorophenyl)isoxazole-3-carbonyl chloride, in place of 4-chloro-5-(4-(trifluoromethyl)phenyl) isoxazole-3-carbonyl chloride gave the title compound. MS (ESI) m/z (M+H$^+$): 353.0/355.0.

The following compounds were prepared according to Example (AE):

Example 13 (AF)

4-Chloro-5-(4-chlorophenyl)-N-cyclobutylisoxazole-3-carboxamide

MS (ESI) m/z (M+H$^+$): 311.1.

Example 13 (AG)

(R)-4-Chloro-5-(4-chlorophenyl)-N-(tetrahydrofuran-3-yl)isoxazole-3-carboxamide

MS (ESI) m/z (M+H$^+$): 327.1/329.1.

Example 13 (AH)

4-Chloro-5-(4-chlorophenyl)-N-isobutylisoxazole-3-carboxamide

MS (ESI) m/z (M+H$^+$): 313.2.

Example 13 (AI)

4-Chloro-5-(4-chlorophenyl)-N-(cyclopropylmethyl)isoxazole-3-carboxamide

MS (ESI) m/z (M+H$^+$): 311.1/313.1.

Example 13 (AJ)

4-Chloro-5-(3,4-difluorophenyl)-N-((1S,3R)-3-(hydroxymethyl)cyclopentyl)isoxazole-3-carboxamide A: 4-Chloro-5-(3,4-difluorophenyl)isoxazole-3-carbonyl chloride The title compound was prepared according to Example 6; Steps A-C.

B: 4-Chloro-5-(3,4-difluorophenyl)-N-((1S,3R)-3-(hydroxymethyl)cyclopentyl) isoxazole-3-carboxamide Using 4-chloro-5-(3,4-difluorophenyl)isoxazole-3-carbonyl chloride, in place of 4-chloro-5-(4-(trifluoromethyl)phenyl)isoxazole-3-carbonyl chloride gave the title compound. MS (ESI) m/z (M+H$^+$): 357.1/359.1.

The following compounds were prepared according to Example 13 (AJ):

Example 13 (AK)

4-Chloro-N-cyclopentyl-5-(3,4-difluorophenyl)isoxazole-3-carboxamide

MS (ESI) m/z (M+H$^+$): 327.1/329.1.

Example 13 (AL)

4-Chloro-5-(3,4-difluorophenyl)-N-((1R,3S)-3-hydroxycyclopentyl)isoxazole-3-carboxamide MS (ESI) m/z (M+H$^+$): 343.0/345.0.

Example 13 (AM)

4-Chloro-5-(3,4-difluorophenyl)-N-((1R,2S)-2-(hydroxymethyl)cyclohexyl)isoxazole-3-carboxamide MS (ESI) m/z (M+H$^+$): 371.0/373.1.

Example 13 (AN)

4-Chloro-N-cyclobutyl-5-(3,4-difluorophenyl)isoxazole-3-carboxamide

MS (ESI) m/z (M+H$^+$): 313.1/315.0.

Example 13 (AO)

4-Chloro-5-(4-chloro-3-fluorophenyl)-N-((1R,3S)-3-hydroxycyclohexyl)isoxazole-3-carboxamide A: 4-Chloro-5-(4-chloro-3-fluorophenyl)isoxazole-3-carboxylic acid The title compound was prepared according to Example 5 (D); Steps A-B.

B: 4-Chloro-5-(4-chloro-3-fluorophenyl)isoxazole-3-carbonyl chloride

The title compound was prepared according to Example 12; Steps E.

D: 4-Chloro-5-(4-chloro-3-fluorophenyl)-N-((1R,3S)-3-hydroxycyclohexyl)isoxazole-3-carboxamide Using 4-chloro-5-(4-chloro-3-fluorophenyl)isoxazole-3-carbonyl chloride, in place of 4-chloro-5-(4-(trifluoromethyl)phenyl)isoxazole-3-carbonyl chloride gave the title compound.

MS (ESI) m/z (M+H$^+$): 372.9/374.9.

Example 14

4-Fluoro-N-((1R,3S)-3-hydroxycyclohexyl)-5-(4-(trifluoromethyl)phenyl)isoxazole-3-carboxamide A: Ethyl 4-fluoro-5-(4-(trifluoromethyl)phenyl)isoxazole-3-carboxylate A mixture of ethyl-5-(4-(trifluoromethyl)phenyl)isoxazole-3-carboxylate (0.96 g, 3.37 mmol), Selectfluor (1.25 g, 3.53 mmol), and tetramethylene sulfone (7.5 g, 62.5 mmol) was heated to 120° C. for 8 hours. After cooling to room temperature, the reaction mixture was diluted with water, stirred for 5 minutes and the resulting white crystals were collected, washed with water and purified by silica gel chromatography eluting with dichloromethane to obtain the title compound (147 mg, 0.53 mmol).

B: 4-Fluoro-5-(4-(trifluoromethyl)phenyl)isoxazole-3-carboxylic acid

To a solution of ethyl 4-fluoro-5-(4-(trifluoromethyl)phenyl)isoxazole-3-carboxylate (147 mg, 0.48 mmol) in tetrahydrofuran (2.5 mL) was added a solution of lithium hydroxide (20 mg, 0.83 mmol) in water (2.5 mL). After stirring for one hour, the reaction mixture was acidified to pH=2 with 1M HCl, and extracted three times with dichloromethane. The dichloromethane extracts were combined, dried over sodium sulfate and rotoevaporated to obtain the title compound (130 mg, 0.47 mmol).

C: 4-Fluoro-N-((1R,3S)-3-hydroxycyclohexyl)-5-(4-(trifluoromethyl)phenyl)isoxazole-3-carboxamide To a solution of 4-fluoro-5-(4-(trifluoromethyl)phenyl)isoxazole-3-carboxylic acid (19 mg, 0.07 mmol), (1S,3R)-3-aminocyclohexanol (9.3 mg, 0.081 mmol), 1-hydroxybenzotriazole hydrate (9.0 mg, 0.07 mmol), and triethylamine (10 μL, 0.07 mmol) in tetrahydrofuran (1 mL) was added N-(3-dimethylaminopropyl)-N'-ethylcarbodiimide hydrochloride (15 mg. 0.081 mmol). After stirring overnight, the volatiles were removed in vacuo and the compound was purified by silica gel chromatography eluting with 5% methanol in dichloromethane to afford the title compound: (12.1 mg, 0.03 mmol). MS (ESI) m/z (M+H$^+$): 373.2.

The method of Example 14 was further used to prepare the following compounds using alternative amines instead of (1S,3R)-3-aminocyclohexanol:

Example 15 (A)

N-Cyclopentyl-4-fluoro-5-(4-(trifluoromethyl)phenyl)isoxazole-3-carboxamide

MS (ESI) m/z (M+H$^+$): 343.2.

Example 15 (B)

cis-4-Fluoro-N-(3-hydroxycyclohexyl)-5-(4-(trifluoromethyl)phenyl)isoxazole-3-carboxamide MS (ESI) m/z (M+H$^+$): 373.3

Example 15 (C)

4-Fluoro-N-((1R,3S)-3-hydroxycyclopentyl)-5-(4-(trifluoromethyl)phenyl)isoxazole-3-carboxamide MS (ESI) m/z (M+H$^+$): 359.3.

Example 16

Racemic-trans-4-chloro-N-(3-hydroxy-6-methoxy-2,3-dihydro-1H-inden-1-yl)-5-(4-(trifluoromethyl)phenyl)isoxazole-3-carboxamide A: 2,2,2-trifluoro-N-(6-methoxy-3-oxo-2,3-dihydro-1H-inden-1-yl)acetamide A solution of 3-amino-3-(3-methoxyphenyl)propanoic acid (2.0 g, 10.0 mmol) in trifluoroacetic acid (15 mL) was stirred for 15 minutes. Trifluoroacetic anhydride (15 mL) was added and the reaction mixture was heated to reflux for 3 hours. The volatiles were removed in vacuo, the residue was triturated with water and the resulting yellow solid was collected by vacuum filtration. Recrystallization with diethyl ether yielded 2,2,2-trifluoro-N-(6-methoxy-3-oxo-2,3-dihydro-1H-inden-1-yl)acetamide (1.3 g, 4.8 mmol). $^1$H-NMR (300 MHz, DMSO-d$_6$) δ ppm: 9.95 (bd, 1H), 7.62 (m, 1H), 7.05 (m, 2H), 5.60 (m, 1H), 3.88 (s, 3H), 3.05 (dd, 1H), 2.55 (m, 1H).

B: trans-2,2,2-trifluoro-N-(-3-hydroxy-6-methoxy-2,3-dihydro-1H-inden-1-yl)acetamide Sodium borohydride (20 mg, 0.51 mmol) was added to a solution of 2,2,2-trifluoro-N-(6-methoxy-3-oxo-2,3-dihydro-1H-inden-1-yl)acetamide (140 mg, 0.51 mmol) in anhydrous methanol (4 mL). After stirring overnight, the volatiles were removed in vacuo and the crude material purified by silica gel chromatography, eluting with 5% methanol in dichloromethane furnished as the first eluting isomer cis-2,2,2-trifluoro-N-(-3-hydroxy-6-methoxy-2,3-dihydro-1H-inden-1-yl)acetamide; (60 mg, 0.22 mmol) $^1$H-NMR (300 MHz, CDCl$_3$) δ 7.34 (d, 1H), 7.01-6.82 (m, 3H), 5.35 (m, 1H), 5.15 (m, 1H), 3.82 (s, 3H), 2.87 (m, 1H), 1.93 (m, 1H).

Followed by the title compound trans-2,2,2-trifluoro-N-(-3-hydroxy-6-methoxy-2,3-dihydro-1H-inden-1-yl)acetamide as the second eluting isomer; (35 mg, 0.13 mmol):
$^1$H-NMR (300 MHz, CDCl$_3$) δ 7.37 (d, 1H), 6.94 (m, 1H), 6.82 (m, 1H), 6.40 (bm, 1H), 5.69 (m, 1H), 5.34 (m, 1H) 3.85 (s, 3H), 2.61 (m, 1H), 2.29 (m, 1H).

C: trans-3-amino-5-methoxy-2,3-dihydro-1H-inden-1-ol

Potassium carbonate (16 mg, 0.116 mmol) was added to a solution of trans-2,2,2-trifluoro-N-(-3-hydroxy-6-methoxy-2,3-dihydro-1H-inden-1-yl)acetamide (32 mg, 0.116 mmol) in methanol (2 mL) and water (1 mL). After stirring for 72 hours, the reaction mixture was diluted with methanol, filtered through a cotton plug, and concentrated in vacuo. The crude compound was purified by silica gel chromatography, eluting with 10% methanol in dichloromethane with 0.1% NH$_4$OH to give the title compound (17 mg, 0.09 mmol). MS (ESI) m/z (M+H$^+$): 180.2

D: Racemic-trans-4-chloro-N-(3-hydroxy-6-methoxy-2,3-dihydro-1H-inden-1-yl)-5-(4-(trifluoromethyl)phenyl)isoxazole-3-carboxamide The title compound was prepared using the procedure of Example 12.
$^1$H-NMR (300 MHz, CDCl$_3$) δ 8.18 (d, 2H), 7.80 (d, 2H), 7.39 (d, 1H), 6.95 (m, 3H), 5.90 (m, 1H), 5.38 (m, 1H), 3.82 (s, 3H), 2.68 (m, 1H), 2.35 (m, 1H).

Example 17

Racemic-cis-4-chloro-N-(3-hydroxy-6-methoxy-2,3-dihydro-1H-inden-1-yl)-5-(4-(trifluoromethyl)phenyl)isoxazole-3-carboxamide The title compound was prepared according to Example 16.
$^1$H-NMR (300 MHz, CDCl$_3$) δ 8.15 (d, 2H), 7.80 (d, 2H), 7.39 (d, 1H), 7.30 (m, 1H), 6.95 (m, 2H), 5.51 (m, 1H), 5.20 (m, 1H), 3.81 (s, 3H), 3.02 (q, 1H), 2.00 (m, 1H).

Example 18

4-Chloro-5-(4-fluorophenyl)-N-(3-oxocyclohexyl) isoxazole-3-carboxamide

A solution of oxalyl chloride (30 μL, 0.34 mmol) in dichloromethane (1 mL) was cooled to −78° C. A solution of dimethylsulfoxide (48 μL, 0.675 mmol) in dichloromethane (0.5 mL) was added drop wise and the mixture was stirred for 5 minutes at −78° C. A solution of 4-chloro-5-(4-fluorophenyl)-N-(3-hydroxycyclohexyl)isoxazole-3-carboxamide (104 mg, 0.307 mmol) in tetrahydrofuran (3 mL) and (0.5 mL) dichloromethane was added over 5 minutes and the reaction mixture was to stirred for 15 minutes at −78° C. Triethylamine (0.215 mL, 1.53 mmol) was added and the reaction was stirred for 10 minutes at −78° C., then allowed to warm to room temperature and stir for an additional 20 minutes. Water was added and the mixture was extracted three times with dichloromethane. The combined organic extracts were dried over $MgSO_4$, filtered, concentrated in vacuo, and purified by silica gel chromatography, eluting with 2% methanol in dichloromethane to give the title compound (19.7 mg, 0.058 mmol). MS (ESI) m/z (M+H$^+$): 337.2/339.2

Example 19

(R)-4-Chloro-N-(3-oxocyclopentyl)-5-(4-(trifluoromethyl)phenyl)isoxazole-3-carboxamide The title compound was prepared according to Example 18.
$^1$H-NMR (300 MHz, CDCl$_3$) δ 8.17 (d, 2H), 7.80 (d, 2H), 6.87 (bd, 1H), 4.71 (m, 1H) 2.71 (dd, 1H), 2.61-2.41 (m, 2H), 2.40-2.25 (m, 2H), 2.08 (m, 1H).

Example 20

(R)-4-Chloro-N-(3-(hydroxyimino)cyclopentyl)-5-(4-(trifluoromethyl)phenyl)isoxazole-3-carboxamide cis/trans mix A suspension of (R)-4-chloro-N-(3-oxocyclopentyl)-5-(4-(trifluoromethyl)phenyl) isoxazole-3-carboxamide (20 mg, 0.054 mmol), hydroxylamine hydrochloride (5 mg, 0.064 mmol), and sodium bicarbonate (7 mg, 0.083 mmol) in ethanol (2 mL) was heated to reflux overnight. The reaction mixture was diluted with ethanol/dichloromethane, filtered through a cotton plug and evaporated in vacuo. Purification by silica gel chromatography, eluting with 8% methanol in dichloromethane gave the title compound as a mixture of cis and trans isomers (10.5 mg, 0.027 mmol). MS (ESI) m/z (M+H$^+$): 388.2/390.3

Example 21

4-Chloro-N-((1R,3R,5S)-3,5-dihydroxycyclohexyl)-5-(4-(trifluoromethyl)phenyl) isoxazole-3-carboxamide A: 4-Chloro-N-((1R,3R,5S)-3,5-dimethoxycyclohexyl)-5-(4-(trifluoromethyl)phenyl) isoxazole-3-carboxamide The title compound was prepared according to Example 12; Steps A-F.

B: 4-Chloro-N-((1R,3R,5S)-3,5-dihydroxycyclohexyl)-5-(4-(trifluoromethyl)phenyl) soxazole-3-carboxamide To a solution of 4-chloro-N-((1R,3R,5S)-3,5-dimethoxycyclohexyl)-5-(4-(trifluoromethyl)phenyl)isoxazole-3-carboxamide (35 mg, 0.08 mmol) in anhydrous MeCN (5 mL) was added iodotrimethylsilane (80 μL, 0.56 mmol). After heating at 60° C. for 40 minutes, the reaction was cooled and poured over ice. Upon melting, the resulting aqueous mixture was extracted three times with dichloromethane. The combined dichloromethane extractions were washed successively with 10% $Na_2S_2O_3$ and brine, dried over $MgSO_4$, filtered and concentrated in vacuo. The crude material was purified by silica gel chromatography, eluting with 10% methanol in dichloromethane gave the title compound (16.6 mg, 0.041 mmol). $^1$H-NMR (300 MHz, CDCl$_3$+30% CD$_3$OD) δ 8.02 (d, 2H), 7.92 (d, 1H), 7.66 (d, 2H), 3.85 (m, 1H), 3.56 (m, 2H), 2.10 (m, 3H), 1.25 (m, 3H).

Example 22

(1S,3R)-3-(4-Chloro-5-(4-(trifluoromethyl)phenyl) isoxazole-3-carboxamido)cyclopentyl 2-aminoacetate A: (1S,3R)-3-(4-chloro-5-(4-(trifluoromethyl)phenyl)isoxazole-3-carboxamido) cyclopentyl 2-(tert-butoxycarbonyl)acetate 4-Chloro-N-((1R,3S)-3-hydroxycyclopentyl)-5-(4-(trifluoromethyl)phenyl) isoxazole-3-carboxamide (57 mg, 152 μmol) was dissolved in tetrahydrofuran (2 mL) at room temperature and treated with Boc-Gly-OH (28 mg, 160 μmol), 1-Hydroxybenzotriazole hydrate (21 mg, 155 μmol), N-(3-dimethylaminopropyl)-N'-ethylcarbodiimide hydrochloride (34 mg, 177 μmol) and triethylamine (21 μL, 151 μmol). The mixture was stirred overnight and the volatiles were then removed in vacuo. The crude residue was purified by silica gel chromatography, eluting with 55% ethylacetate in hexanes to give the title compound (1S,3R)-3-(4-chloro-5-(4-(trifluoromethyl)phenyl)isoxazole-3-carboxamido)cyclopentyl 2-(tert-butoxycarbonyl)acetate (25 mg, 47 μmol).

B: (1S,3R)-3-(4-Chloro-5-(4-(trifluoromethyl)phenyl)isoxazole-3-carboxamido)cyclopentyl 2-aminoacetate (1S,3R)-3-(4-chloro-5-(4-(trifluoromethyl)phenyl)isoxazole-3-carboxamido) cyclopentyl 2-(tert-butoxycarbonyl)acetate (20 mg, 37.6 μmol) was treated with hydrochloric acid (4.0 M in 1,4-Dioxane, 3 mL) for 1 hour. The volatiles were removed in vacuo to give the title compound as the hydrochloride salt (16 mg, 34 μmol). MS (ESI) m/z (M+H+): 432.2.

Example 23

4-Chloro-5-(3-fluoro-4-(trifluoromethyl)phenyl)-N-(tetrahydro-2H-pyran-4-yl)isoxazole-3-carboxamide A: Ethyl 5-(3-fluoro-4-(trifluoromethyl)phenyl)isoxazole-3-carboxylate The title compound was prepared according to Example 1; Steps A-B, whereby, in Step A, 3-fluoro-4-(trifluoromethyl) acetophenone was used instead of 4-chloroacetophenone.

B: (5-(3-Fluoro-4-(trifluoromethyl)phenyl)isoxazol-3-yl)methanol

To a solution of ethyl 5-(3-fluoro-4-(trifluoromethyl)phenyl)isoxazole-3-carboxylate (2.0 g, 6.60 mmol) in tetrahydrofuran (25 mL) was added lithium aluminium hydride (375 mg, 9.89 mmol) and the reaction mixture was stirred for 2 hours at room temperature. The reaction was quenched by the addition of water (0.18 mL) followed by an aqueous solution of 1N NaOH (0.18 mL) and finally water (0.54 mL) over a 30 minute period. The resultant viscous grey slurry was diluted with diethyl ether (50 mL) and stirred for 30 minutes before filtering through a celite pad. The cake was washed with diethyl ether (3×70 mL) and the filtrate evaporated to dryness in vacuo to obtain (5-(3-fluoro-4-(trifluoromethyl)phenyl)isoxazol-3-yl)methanol (1.43 g, 5.48 mmol).

C: (4-Chloro-5-(3-fluoro-4-(trifluoromethyl)phenyl)isoxazol-3-yl)methyl acetate To a solution of (5-(3-fluoro-4-(trifluoromethyl)phenyl)isoxazol-3-yl)methanol (1.4 g, 5.36 mmol) in acetic acid (12 mL), N-chlorosuccinimide (1.07 g, 8.04 mmol) and sulphuric acid (0.6 mL) were added. The reaction mixture was stirred for 5 hours at 120° C. before being allowed to cool and then diluted with water (100 mL). The aqueous reaction mixture was extracted with diethyl ether (3×100 mL), the organics combined, washed with brine, dried with $Na_2SO_4$. The volatiles were removed in vacuo and the resulting residue was purified by silica gel chromatography, eluting with heptane to 20% ethylacetate in heptane, to afford (4-chloro-5-(3-fluoro-4-(trifluoromethyl)phenyl)isoxazol-3-yl)methyl acetate (1 g, 2.96 mmol).

D: (4-Chloro-5-(3-fluoro-4-(trifluoromethyl)phenyl)isoxazol-3-yl)methanol

To a solution of (4-chloro-5-(3-fluoro-4-(trifluoromethyl)phenyl)isoxazol-3-yl)methyl acetate (1 g, 2.96 mmol) in tetrahydrofuran (20 mL) an aqueous solution of 1N LiOH (8.88 mL, 8.88 mmol) was added. The biphasic reaction mixture was stirred vigorously for 3 hours at 60° C., then allowed to cool and left to stand over the weekend. The reaction mixture was transferred to a separating funnel and the organic layer removed. The aqueous layer was extracted with diethyl ether (2×20 mL), the organics were combined, washed with water (20 mL) and brine (20 mL) before drying with $Na_2SO_4$. Filtration and evaporation to dryness in vacuo afforded (4-chloro-5-(3-fluoro-4-(trifluoromethyl)phenyl)isoxazol-3-yl)methanol (878 mg, 2.97 mmol).

E: 4-Chloro-5-(3-fluoro-4-(trifluoromethyl)phenyl)isoxazole-3-carboxylic acid To a stirred solution of (4-chloro-5-(3-fluoro-4-(trifluoromethyl)phenyl)isoxazol-3-yl)methanol (580 mg, 1.96 mmol) and triethylamine (1.930 mL, 13.73 mmol) in dichloromethane (9.6 mL) and DMSO (1.60 mL), sulphur trioxide pyridine complex (1.25 g, 7.85 mmol) was added. The reaction mixture was stirred for 2 hours at room temperature before removal of the volatiles in vacuo. The resultant crude residue was diluted with ethylacetate (20 mL), washed with 2N HCl (30 mL), water (30 mL) and brine (30 mL). The organic phase was dried with $Na_2SO_4$, filtered and evaporated to dryness in vacuo. This crude mixture was dissolved in tBuOH/$H_2O$ (4:1) (20 mL), and to this sodium dihydrogen phosphate dihydrate (1.07 g, 6.87 mmol) and a solution of 2-methyl-2-butene (860 mg, 12.26 mmol) in tetrahydrofuran (5 mL), was added. Finally sodium chlorite (222 mg, 2.45 mmol) was added and the reaction mixture stirred overnight. The reaction mixture was evaporated to dryness, partitioned between ethyl acetate (20 mL) and water (15 mL) and the aqueous phase acidified to pH 4 with acetic acid. The organic layer was removed and then the aqueous layer extracted with ethyl acetate (3×20 mL). The organics were combined, dried with $Na_2SO_4$, filtered and evaporated to dryness in vacuo. The resulting residue was purified by silica gel chromatography, eluting with dichloromethane to 20% methanol/(acetic acid) in dichloromethane, to afford 4-chloro-5-(3-fluoro-4-(trifluoromethyl)phenyl)isoxazole-3-carboxylic acid (0.4 g, 1.29 mmol).

F: 4-Chloro-5-(3-fluoro-4-(trifluoromethyl)phenyl)-N-(tetrahydro-2H-pyran-4-yl)isoxazole-3-carboxamide To a stirred solution of 4-chloro-5-(3-fluoro-4-(trifluoromethyl)phenyl)isoxazole-3-carboxylic acid (45 mg, 0.145 mmol), tetrahydro-2H-pyran-4-amine (14.7 mg, 0.15 mmol) and triethylamine (61.3 µl, 0.44 mmol) in dichloromethane (2 mL) a 50 wt % solution of 1-propanephosphonic acid cyclic anhydride (64.9 µl, 0.22 mmol) in ethylacetate was added. After stirring for 1 hr, the reaction mixture was diluted with dichloromethane (10 mL) washed with $NaHCO_3$ solution (10 mL) and concentrated in vacuo. The resulting residue was purified by silica gel chromatography, eluting with dichloromethane to 20% methanol in dichloromethane to afford the title compound: (18 mg, 0.046 mmol).

MS (ESI) m/z (M+H$^+$): 393.

The method of Example 23 was further used to prepare the following compounds using alternative amines instead of tetrahydro-2H-pyran-4-amine.

Example 24 (A)

4-Chloro-N-cyclopentyl-5-(3-fluoro-4-(trifluoromethyl)phenyl)isoxazole-3-carboxamide MS (ESI) m/z (M+H$^+$): 377.3.

Example 24 (B)

4-Chloro-5-(3-fluoro-4-(trifluoromethyl)phenyl)-N-(3-(hydroxymethyl)phenyl)isoxazole-3-carboxamide MS (ESI) m/z (M+Na$^+$): 438.0.

Example 24 (C)

4-Chloro-5-(3-fluoro-4-(trifluoromethyl)phenyl)-N-(2-(2-hydroxyethyl)phenyl)isoxazole-3-carboxamide MS (ESI) m/z (M+H$^+$): 429.0.

Example 24 (D)

(R)-4-Chloro-5-(3-fluoro-4-(trifluoromethyl)phenyl)-N-(1-hydroxybutan-2-yl)isoxazole-3-carboxamide MS (ESI) m/z (M+H$^+$): 381.0.

Example 24 (E)

(R)-4-Chloro-5-(3-fluoro-4-(trifluoromethyl)phenyl)-N-(1-hydroxy-3-methylbutan-2-yl)isoxazole-3-carboxamide MS (ESI) m/z (M+H$^+$): 395.0.

Example 24 (F)

4-Chloro-5-(3-fluoro-4-(trifluoromethyl)phenyl)-N-((1R,3S)-3-hydroxycyclohexyl) isoxazole-3-carboxamide MS (ESI) m/z (M+H$^+$): 407.0.

Example 24 (G)

cis-4-Chloro-5-(3-fluoro-4-(trifluoromethyl)phenyl)-N-(4-hydroxycyclohexyl)isoxazole-3-carboxamide MS (ESI) m/z (M+H$^+$): 407.0.

Example 24 (H)

4-Chloro-N-(1-cyclopropyl-3-hydroxypropyl)-5-(4-(trifluoromethyl)phenyl)isoxazole-3-carboxamide A: 4-Chloro-5-(4-(trifluoromethyl)phenyl)isoxazole-3-carboxylic acid The title compound was prepared according to Example 12; Steps A-D.

B: 4-Chloro-N-(1-cyclopropyl-3-hydroxypropyl)-5-(4-(trifluoromethyl)phenyl)isoxazole-3-carboxamide Using 4-Chloro-5-(4-(trifluoromethyl)phenyl)isoxazole-3-carboxylic acid, in place of 4-chloro-5-(3-fluoro-4-(trifluoromethyl)phenyl)isoxazole-3-carboxylic acid gave the title compound.
MS (ESI) m/z (M+H$^+$): 389.
The following compounds were prepared according to Example 24 (H):

Example 24 (I)

(S)-4-Chloro-N-(1-methoxypropan-2-yl)-5-(4-(trifluoromethyl)phenyl)isoxazole-3-carboxamide MS (ESI) m/z (M+H$^+$): 363.

Example 24 (J)

4-Chloro-N-(2-hydroxyethyl)-5-(4-(trifluoromethyl)phenyl)isoxazole-3-carboxamide MS (ESI) m/z (M+H$^+$): 335.

Example 24 (K)

(S)-4-Chloro-N-(3-methylbutan-2-yl)-5-(4-(trifluoromethyl)phenyl)isoxazole-3-carboxamide MS (ESI) m/z (M+H$^+$): 361.

Example 24 (L)

4-Chloro-N-(2-hydroxy-2-methylpropyl)-5-(4-(trifluoromethyl)phenyl)isoxazole-3-carboxamide: MS (ESI) m/z (M+H$^+$): 363.

Example 24 (M)

(R)-4-Chloro-N-(6-oxopiperidin-3-yl)-5-(4-(trifluoromethyl)phenyl)isoxazole-3-carboxamide MS (ESI) m/z (M+H$^+$): 388.

Example 24 (N)

4-Chloro-N-((1-(hydroxymethyl)cyclopentyl)methyl)-5-(4-(trifluoromethyl)phenyl) isoxazole-3-carboxamide MS (ESI) m/z (M+H$^+$): 403.

Example 24 (O)

4-Chloro-N-(3-hydroxy-1-phenylpropyl)-5-(4-(trifluoromethyl)phenyl)isoxazole-3-carboxamide MS (ESI) m/z (M+H$^+$): 425.

Example 24 (P)

(R)-4-Chloro-N-(1-hydroxybutan-2-yl)-5-(4-(trifluoromethyl)phenyl)isoxazole-3-carboxamide: MS (ESI) m/z (M+H$^+$): 363.

Example 24 (Q)

4-Chloro-N-((1-(hydroxymethyl)cyclobutyl)methyl)-5-(4-(trifluoromethyl)phenyl) isoxazole-3-carboxamide MS (ESI) m/z (M+H$^+$): 389.1.

Example 24 (R)

4-Chloro-N-((1R,2S)-2-hydroxycyclopentyl)-5-(4-(trifluoromethyl)phenyl)isoxazole-3-carboxamide MS (ESI) m/z (M+H$^+$): 375.

Example 24 (S)

(R)-4-Chloro-N-(tetrahydrofuran-3-yl)-5-(4-(trifluoromethyl)phenyl)isoxazole-3-carboxamide $^1$H-NMR (300 MHz, CDCl$_3$) δ 8.17 (m, 2H), 7.80 (m, 2H), 6.90 (d, 1H), 4.74 (m, 1H), 4.08 (q, 1H), 3.93 (m, 1H), 3.84 (m, 2H), 2.38 (m, 2H), 1.98 (m, 1H).

Example 24 (T)

4-Chloro-N-(3,3-difluorocyclobutyl)-5-(4-(trifluoromethyl)phenyl)isoxazole-3-carboxamide: MS (ESI) m/z (M+H$^+$): 381.1.

Example 24 (U)

4-Chloro-N-(1,1,1-trifluorobutan-2-yl)-5-(4-(trifluoromethyl)phenyl)isoxazole-3-carboxamide MS (ESI) m/z (M+H$^+$): 401.1.

Example 24 (V)

4-Chloro-N-(2-cyclopropylethyl)-5-(4-(trifluoromethyl)phenyl)isoxazole-3-carboxamide MS (ESI) m/z (M+H$^+$): 359.

Example 24 (W)

4-Chloro-N-(cyclobutylmethyl)-5-(4-(trifluoromethyl)phenyl)isoxazole-3-carboxamide MS (ESI) m/z (M+H$^+$): 359.

Example 24 (X)

(R)—N-sec-Butyl-4-chloro-5-(4-(trifluoromethyl)phenyl)isoxazole-3-carboxamide

MS (ESI) m/z (M+H$^+$): 347.

Example 24 (Y)

(S)-4-Chloro-5-(4-(trifluoromethyl)phenyl)-N-(1,1,1-trifluoropropan-2-yl)isoxazole-3-carboxamide MS (ESI) m/z (M+H$^+$): 387.

The following compounds were prepared according to Example 23:

Example 24 (Z)

4-Chloro-5-(3-fluoro-4-(trifluoromethyl)phenyl)-N-((1R,2S)-2-hydroxycyclopentyl)isoxazole-3-carboxamide MS (ESI) m/z (M+H$^+$): 393.

Example 24 (AA)

(R)-4-Chloro-5-(3-fluoro-4-(trifluoromethyl)phenyl)-N-(tetrahydrofuran-3-yl)isoxazole-3-carboxamide MS (ESI) m/z (M+H$^+$): 379.

Example 25

N-Cyclopentyl-4-ethyl-5-(4-(trifluoromethyl)phenyl)isoxazole-3-carboxamide

A: 4-Bromo-N-cyclopentyl-5-(4-(trifluoromethyl)phenyl)isoxazole-3-carboxamide

The title compound was prepared according to Example 10 (M); Steps A-D.

B: N-Cyclopentyl-5-(4-(trifluoromethyl)phenyl)-4-vinylisoxazole-3-carboxamide

Tetrakis(triphenylphosphine)palladium (0) (57.9 mg, 0.05 mmol) was added to a stirred suspension of 2,4,6-trivinylcyclotriboroxane pyridine complex (121 mg, 0.50 mmol), 4-bromo-N-cyclopentyl-5-(4-(trifluoromethyl)phenyl)isoxazole-3-carboxamide (202 mg, 0.50 mmol) and potassium carbonate (138 mg, 1.0 mmol) in DME (4.7 mL) and water (1.6 mL) and heated to 100° C. for 2 hours. The reaction mixture was allowed to cool to room temperature and partitioned between water and ethylacetate. The organics were dried over magnesium sulphate and concentrated in vacuo. Purification by silica gel chromatography eluting with heptane to 20% ethylacetate in heptane to obtain N-cyclopentyl-5-(4-(trifluoromethyl)phenyl)-4-vinylisoxazole-3-carboxamide (140 mg, 0.40 mmol).

C: N-Cyclopentyl-4-ethyl-5-(4-(trifluoromethyl)phenyl)isoxazole-3-carboxamide

To a stirred solution of N-cyclopentyl-5-(4-(trifluoromethyl)phenyl)-4-vinylisoxazole-3-carboxamide (70 mg, 0.2 mmol) in ethanol (2 mL), palladium on carbon (5%) (5 mg) was added and the reaction mixture was then placed under a hydrogen atmosphere (balloon) for 2 hours. After this time the crude mixture was filtered through celite and concentrated in vacuo. Purification by silica gel chromatography eluting with heptane increasing to heptane to 15% ethylacetate in heptane afforded the title compound (36 mg, 0.1 mmol).

MS (ESI) m/z (M+H$^+$): 353.

The method of Example 25 was further used to prepare the following compound using cis-propenylboronic acid instead of 2,4,6-trivinylcyclotriboroxane pyridine complex:

Example 26

N-Cyclopentyl-4-propyl-5-(4-(trifluoromethyl)phenyl)isoxazole-3-carboxamide

MS (ESI) m/z (M+H$^+$): 367.

Example 27

A: 4-Chloro-5-(4-(trifluoromethyl)phenyl)isoxazole-3-carboxylic acid

The title compound was prepared according to Example 12; Steps A-D.

B: Cis-4-Chloro-N-(4-hydroxycyclohexyl)-5-(4-(trifluoromethyl)phenyl)isoxazole-3-carboxamide To a stirred suspension of 4-chloro-5-(4-(trifluoromethyl)phenyl)isoxazole-3-carboxylic acid (50 mg, 0.17 mmol) in acetonitrile (2 mL) was added O-(7-azabenzotriazol-1-yl)-N, N,N',N'-tetramethyluronium hexafluorophosphate (85 mg, 0.22 mmol), followed by cis-4-aminocyclohexanol hydrochloride (26 mg, 0.17 mmol). Triethylamine (52 mg, 0.51 mmol) was added before heating in the microwave at 150° C. for 10 minutes. After 10 minutes, the solvent was removed in vacuo, and the residue was partitioned between water and dichloromethane. The aqueous layer was separated and extracted with dichloromethane (3×10 mL), the combined organic extracts were dried with MgSO$_4$, filtered and the solvent removed in vacuo. The residue was purified by preparative HPLC to afford the title compound: (26 mg, 0.067 mmol).

MS (ESI) m/z (M+H$^+$): 389.9

The method of Example 27 was further used to prepare the following compound using alternative amines instead of cis-4-aminocyclohexanol hydrochloride.

Example 28 (A)

Racemic-4-Chloro-N-(cis-2-hydroxycyclohexyl)-5-(4-(trifluoromethyl)phenyl)isoxazole-3-carboxamide MS (ESI) m/z (M+H$^+$): 390

Example 29 (B)

4-Chloro-5-(4-chloro-3-fluorophenyl)-N-((1R,3S)-3-hydroxycyclohexyl)isoxazole-3-carboxamide A: 4-Chloro-5-(4-chloro-3-fluorophenyl)isoxazole-3-carboxylic acid The title compound was prepared according to Example 5 (D); Steps A-B.

B: 4-Chloro-5-(4-chloro-3-fluorophenyl)-N-((1R,3S)-3-hydroxycyclohexyl)isoxazole-3-carboxamide Using 4-Chloro-5-(4-chloro-3-fluorophenyl)isoxazole-3-carboxylic acid, in place of 4-Chloro-5-(4-(trifluoromethyl)phenyl)isoxazole-3-carboxylic acid gave the title compound.

MS (ESI) m/z (M+H$^+$): 373.

Example 30

5-(3-Fluoro-4-(trifluoromethyl)phenyl)-4-methyl-N-(tetrahydro-2H-pyran-4-yl)isoxazole-3-carboxamide A: Ethyl 5-(3-fluoro-4-(trifluoromethyl)phenyl)-4-methylisoxazole-3-carboxylate Tetrakis(triphenylphosphine)palladium(0) (139 mg, 0.121 mmol) was added to a suspension of 2-(3-fluoro-4-(trifluoromethyl)phenyl)-4,4,5,5-tetramethyl-1,3,2-dioxaborolane (350 mg, 1.21 mmol), ethyl 5-bromo-4-methylisoxazole-3-carboxylate (282 mg, 1.21 mmol) and potassium carbonate (334 mg, 2.413 mmol) in DME and water mix. The reaction mixture was sealed in a microwave vial and heated at 100° C. for 2 hours, after which time, the reaction was allowed to cool. The reaction mixture was then diluted with ethyl acetate and washed with water. The aqueous layer was then extracted with ethyl acetate, the organics combined, washed with brine and dried over magnesium sulfate, filtered and concentrated in vacuo. the resulting residue was purified by silica gel chromatography, eluting with heptane to 40% ethylacetate in heptane, to afford ethyl 5-(3-fluoro-4-(trifluoromethyl)phenyl)-4-methylisoxazole-3-carboxylate (196 mg, 0.62 mmol).

B: 5-(3-Fluoro-4-(trifluoromethyl)phenyl)-4-methylisoxazole-3-carboxylic acid

The title compound was prepared using the procedure of Example 3; Step A whereby LiOH was used instead of NaOH.

C: 5-(3-Fluoro-4-(trifluoromethyl)phenyl)-4-methylisoxazole-3-carbonyl chloride

The title compound was prepared using the procedure of Example 3; Step B.

D: 5-(3-Fluoro-4-(trifluoromethyl)phenyl)-4-methyl-N-(tetrahydro-2H-pyran-4-yl)isoxazole-3-carboxamide The title compound was prepared using the procedure of Example 3; Step C whereby triethylamine was used in place of potassium carbonate.

MS (ESI) m/z (M+H$^+$): 373.

The method of Example 30 was further used to prepare the following compounds:

Example 31 (A)

5-(3-Fluoro-4-(trifluoromethyl)phenyl)-N-((1R,3S)-3-hydroxycyclohexyl)-4-methylisoxazole-3-carboxamide MS (ESI) m/z (M+H$^+$): 387.

Example 31 (B)

5-(3-Fluoro-4-(trifluoromethyl)phenyl)-N-(2-hydroxyethyl)-4-methylisoxazole-3-carboxamide: MS (ESI) m/z (M+H$^+$): 333.

Example 31 (C)

(R)-5-(3-Fluoro-4-(trifluoromethyl)phenyl)-N-(1-hydroxybutan-2-yl)-4-methylisoxazole-3-carboxamide MS (ESI) m/z (M+H$^+$): 361.1.

Example 31 (D)

(R)-5-(3-Fluoro-4-(trifluoromethyl)phenyl)-N-(1-hydroxy-3-methylbutan-2-yl)-4-methylisoxazole-3-carboxamide MS (ESI) m/z (M+H$^+$): 375.2.

Example 31 (E)

(S)-5-(3-Fluoro-4-(trifluoromethyl)phenyl)-4-methyl-N-(3-methylbutan-2-yl)isoxazole-3-carboxamide MS (ESI) m/z (M+H$^+$): 359.2.

Example 31 (F)

N-(3,3-Difluorocyclobutyl)-5-(3-fluoro-4-(trifluoromethyl)phenyl)-4-methylisoxazole-3-carboxamide $^1$H-NMR (300 MHz, CDCl$_3$) δ 7.78 (m, 1H), 7.60 (m, 2H), 7.05 (d, 1H), 4.45 (m, 1H), 3.12 (m, 2H), 2.65 (m, 2H), 2.50 (s, 3H).

Example 31 (G)

N-Cyclopentyl-5-(3-fluoro-4-(trifluoromethyl)phenyl)-4-methylisoxazole-3-carboxamide MS (ESI) m/z (M+H$^+$): 357.2.

Example 31 (H)

5-(4-Chloro-2-ethoxyphenyl)-N-((1R,3S)-3-hydroxycyclohexyl)-4-methylisoxazole-3-carboxamide

A: Ethyl 5-(4-chloro-2-ethoxyphenyl)-4-methylisoxazole-3-carboxylate

The title compound was prepared according to Example 30; Step A, whereby 4-chloro-2-ethoxyphenylboronic acid was used in place of 2-(3-fluoro-4-(trifluoromethyl)phenyl)-4,4,5,5-tetramethyl-1,3,2-dioxaborolane.

B: 5-(4-Chloro-2-ethoxyphenyl)-4-methylisoxazole-3-carboxylic acid

The title compound was prepared according to Example 30; Step B, whereby ethyl 5-(4-chloro-2-ethoxyphenyl)-4-methylisoxazole-3-carboxylate was used in place of ethyl 5-(3-fluoro-4-(trifluoromethyl)phenyl)-4-methylisoxazole-3-carboxylate.

C: 5-(4-chloro-2-ethoxyphenyl)-4-methylisoxazole-3-carbonyl chloride

The title compound was prepared according to Example 30; Step B, whereby 5-(4-chloro-2-ethoxyphenyl)-4-methylisoxazole-3-carboxylic acid was used in place of 5-(3-fluoro-4-(trifluoromethyl)phenyl)-4-methylisoxazole-3-carboxylic acid.

D: 5-(4-Chloro-2-ethoxyphenyl)-N-((1R,3S)-3-hydroxycyclohexyl)-4-methylisoxazole-3-carboxamide The title compound was prepared according to Example 30.
MS (ESI) m/z (M+H$^+$): 379.1.

Example 31 (I)

Racemic-5-(4-Chloro-2-ethoxyphenyl)-N-(cis-2-hydroxycyclohexyl)-4-methylisoxazole-3-carboxamide The title compound was prepared according to Example 30 (H).
MS (ESI) m/z (M+H$^+$): 379.1.

Example 32

5-(4-tert-Butylphenyl)-4-chloro-N-cyclopentylisoxazole-3-carboxamide

A: Ethyl 4-(4-tert-butylphenyl)-2,4-dioxobutanoate

To a cooled solution, <5° C., of sodium ethoxide (4.4 g, 64.6 mmol) in ethanol, diethyl oxalate (7.71 mL, 56.7 mmol) in toluene (150 mL) was added. The reaction mixture was stirred for 30 min, before the addition of 1-(4-tert-butylphenyl)ethanone (56.7 mmol, 10 g) dropwise in toluene (20 mL) (via pressurised dropping funnel). The reaction mixture was stirred overnight to room temperature and then evaporated to low volume. Acetic acid was added and the resultant precipitate was filtered and washed with heptane to obtain ethyl 4-(4-tert-butylphenyl)-2,4-dioxobutanoate (15.68 g, 56.7 mmol).

B: Ethyl 5-(4-tert-butylphenyl)isoxazole-3-carboxylate

Hydroxylamine hydrochloride (6.14 g, 88.0 mmol) was added to a suspension of ethyl 4-(4-tert-butylphenyl)-2,4-dioxobutanoate (20.4 g, 73.7 mmol) in absolute ethanol (300 mL) and the reaction was heated to reflux for 3 hours. After cooling to room temperature, the organics were removed in vacuo and the resulting residue was purified by silica gel chromatography, eluting with heptane to 10% methanol in dichloromethane, to obtain afford the title compound white solid was filtered, washed with water and cold ethanol and dried in vacuo to obtain ethyl 5-(4-tert-butylphenyl)isoxazole-3-carboxylate (15.9 g, 58.0 mmol).

C: Ethyl 5-(4-tert-butylphenyl)-4-chloroisoxazole-3-carboxylate

A mixture of ethyl 5-(4-tert-butylphenyl)isoxazole-3-carboxylate (2.0 g, 7.32 mmol) and N-chlorosuccinimide (2.44 g, 18.3 mmol) in acetic acid (50 mL) was heated to reflux for 3 days. The reaction mixture was then allowed to cool to room temperature, poured over ice and the resulting white solid was collected, dissolved in ethyl acetate and the organics washed with water, brine and dried with sodium sulphate before being filtered, and evaporated in vacuo. The resultant residue was re-dissolved in dichloromethane, this was then extracted with sodium carbonate solution, and dried using a hydrophobic frit. The organics were removed in vacuo to obtain ethyl 5-(4-tert-butylphenyl)-4-chloroisoxazole-3-carboxylate (0.81 g, 2.63 mmol).

D: 5-(4-tert-butylphenyl)-4-chloroisoxazole-3-carboxylic acid

The title compound was prepared using the procedure of Example 3; Step A whereby LiOH was used instead of NaOH.

E: 5-(4-tert-Butylphenyl)-4-chloro-N-cyclopentyl-isoxazole-3-carboxamide

The title compound was prepared using the procedure of Example 24; Step F whereby 5-(4-tert-butylphenyl)-4-chloroisoxazole-3-carboxylic acid was used in place of 4-chloro-5-(4-(trifluoromethyl)phenyl)isoxazole-3-carboxylic acid.
MS (ESI) m/z (M+H$^+$): 347.

The method of Example 32 was further used to prepare the following compound using alternative amines instead of cyclopentylamine.

Example 33 (A)

5-(4-tert-Butylphenyl)-4-chloro-N-(cis-4-hydroxycyclohexyl)isoxazole-3-carboxamide MS (ESI) m/z (M+H$^+$): 377.

Example 32 (B)

5-(4-tert-Butylphenyl)-4-chloro-N-((1S,2R)-2-(hydroxymethyl)cyclohexyl)isoxazole-3-carboxamide MS (ESI) m/z (M+H$^+$): 391.

Example 33 (C)

5-(4-tert-Butylphenyl)-4-chloro-N-(tetrahydro-2H-pyran-4-yl)isoxazole-3-carboxamide MS (ESI) m/z (M+H$^+$): 363.

Example 33 (D)

5-(4-tert-Butylphenyl)-4-chloro-N-cyclobutylisoxazole-3-carboxamide 2,2,2-trifluoroacetate MS (ESI) m/z (M+H$^+$): 333.

Example 33 (E)

5-(4-tert-Butylphenyl)-4-chloro-N-isopropylisoxazole-3-carboxamide 2,2,2-trifluoroacetate MS (ESI) m/z (M+H$^+$): 321.

Example 34

Vanilloid Receptor Binding Assay

Test compounds were prepared as stock solution in dimethylsulfoxide and tested for activity over several log units (ranging 100 μM-100 pM). Compounds were further diluted in assay buffer as necessary for IC$_{50}$ determination.

Chinese hamster ovary cells expressing human VR1 were grown in DMEM/F12 50/50 Mix (Mediatech, Inc., Herndon, Va., USA), supplemented with 10% FetalClone II (Hyclone, Logan, Utah, USA), 1% GlutaMax (Invitrogen Corp., Carlsbad, Calif., USA), 1% Pen/Strep (Mediatech) and 0.4 mg/ml G418 (Mediatech). The day before the assay, cells were seeded into 384-well tissue culture-treated black plates with clear bottoms (Corning, Inc., Corning, N.Y., USA), at 10,000 viable cells/well in 50 μl/well of medium containing no G418.

On the day of the assay, which is the FLIPR® Calcium 3 Assay commercially available from Molecular Devices Corp., Sunnyvale, Calif. USA, the plating medium was removed and replaced with 25 μl/well 1× Calcium 3 Assay kit dye, prepared in VR1 Buffer (160 mM NaCl, 4.5 mM KCl, 10 mM HEPES, 10 mM Glucose, 2 mM CaCl$_2$, 1 mM MgCl$_2$ and 0.5 mM Probenecid). After 1 hour incubation at room temperature, the plates were loaded into the FLIPR (Molecular Devices, Corp.), which adds 12.5 μl of test compound in VR1 Buffer containing 4% dimethylsulfoxide and reads the subsequent change in the fluorescence of the cells to monitor agonist activity. Ten minutes after compound addition, the plates were reloaded into the FLIPR, which adds 12.5 μl of 30 nM capsaicin in VR1 Buffer and reads the subsequent change in the fluorescence of the cells to monitor antagonist activity. In this way, the same assay was used to assess both the agonist activity and antagonist activity of test compounds.

Typical IC$_{50}$ values measured in the in vitro assay described above for the compounds of the invention are 5 μM or less. For several embodiments of the invention the IC$_{50}$ was found to be below 100 nM.

A representative set of compounds with corresponding functional data, displayed as either pEC50 or % Mean effect seen at the highest concentration of 10 μM, can be seen in the table below:

| Compound | TRPV1 pEC50 | TRPV1 % Mean effect at 10 μM concentration |
|---|---|---|
| 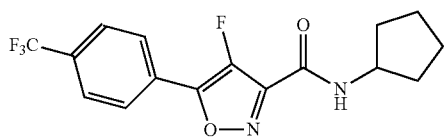<br>Example 15A | 7.5 | 96 |
| 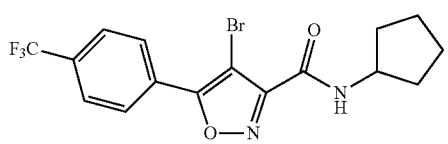<br>Example 10M | 8.0 | 67 |

-continued
| Compound | TRPV1 pEC50 | TRPV1 % Mean effect at 10 μM concentration |
|---|---|---|
| 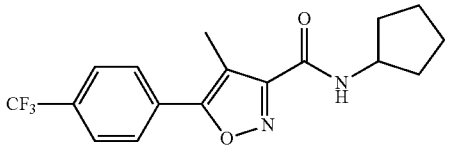 Example 2L | 7.4 | 101 |
| 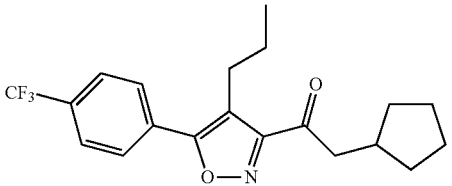 Example 26 | 7.0 | 98 |
| 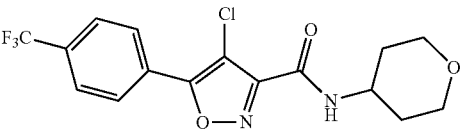 Example 2C | 7.5 | 89 |
| 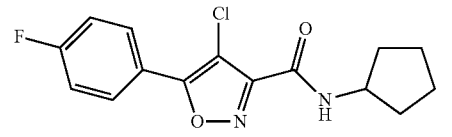 Example 13Y | 7.0 | 98 |
| 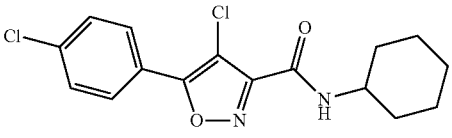 Example 2Q | 7.2 | 88 |
| 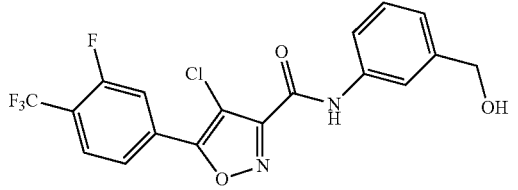 Example 24B | 7.5 | 103 |
| 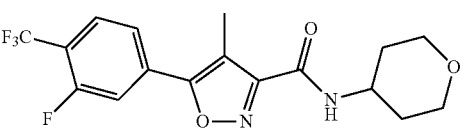 Example 30 | 7.9 | 99 |

-continued

| Compound | TRPV1 pEC50 | TRPV1 % Mean effect at 10 μM concentration |
|---|---|---|
| Example 31C | 7.2 | 99 |
| Example 31E | 7.0 | 103 |
| Example 2H | 8.4 | 90 |
| Example 2A | 7.8 | 102 |
| Example 2P | 6.8 | 89 |
| Reference compound (WO 2007/067710) | 6.3 | 97 |

| Compound | TRPV1 pEC50 | TRPV1 % Mean effect at 10 μM concentration |
|---|---|---|
| Reference compound (WO 2007/067710) | ND | 17 |
| 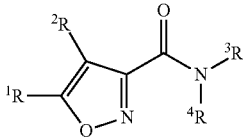 Reference compound (WO 2007/067710) | ND | 50 |

ND reflects that due to the low TRPV1 antagonist activity within this assay, no pEC50 could be determined.

What is claimed:

1. An isoxazole-3-carboxamide derivative having the general Formula I

Formula 1 wherein
- $R_1$ is phenyl, each of which optionally substituted by 1-3 substituents selected from halogen, $(C_{1-4})$alkyl and $(C_{1-4})$alkyloxy, the alkyl and alkyloxy group being optionally substituted with halogen;
- $R_2$ is $(C_{1-3})$alkyl, $(C_{3-8})$cycloalkyl, cyano or halogen, provided that when $R_2$ is cyano $R_3$ is not phenyl;
- $R_3$ is $(C_{1-8})$alkyl, $(C_{2-8})$alkenyl, or $(C_{2-8})$alkynyl, each of which optionally substituted by one or 2 substituents independently selected from halogen, hydroxy and phenyl, optionally substituted by hydroxy or amino; or
- $R_3$ is $(C_{3-10})$cycloalkyl, $(C_{3-8})$cycloalkenyl or $(C_{3-8})$cycloalkyl$(C_{1-3})$alkyl, each cycloalkyl group may be fused to a benzo group, and each cycloalkyl group may be substituted by oxo, hydroxyimino, amino, hydroxy, carboxy, cyano, $(C_{1-3})$alkyl or hydroxy$(C_{1-3})$alkyl; or
- $R_3$ is a saturated 4-8-membered heterocyclic ring containing 1 or 2 heteroatoms selected from $NR_5$, O, S and $SO_2$, optionally substituted by hydroxyl or oxo; or
- $R_3$ is phenyl, naphthyl or pyridyl, each of which may be fused to a 5- or 6-membered saturated heterocyclic ring containing 1 or 2 heteroatoms selected from $NR_5$, O and S, and each of which may be substituted by amino, halogen, hydroxy, hydroxyimino, oxo, mercapto, $(C_{1-3})$-alkyl, $(C_{1-3})$-alkyloxy or hydroxy$(C_{1-3})$alkyl, each alkyl group optionally substituted by one or more halogens; or
- $R_3$ is a bicyclic heteroaromatic ring system containing 1-3 heteroatoms selected from N, O and S, which may be substituted by hydroxy, amino, $(C_{1-3})$alkyl or hydroxy-$(C_{1-3})$alkyl;
- $R_4$ is H or $(C_{1-4})$alkyl; or
- $R_4$ together with $R_3$ and the N to which they are bonded form a saturated 4-8 membered ring, optionally containing a further heteroatom selected from O, S and $SO_2$, the ring being optionally substituted by oxo, hydroxyimino, amino, hydroxy, carboxy, carboxamido, $(C_{1-3})$alkyl, hydroxy$(C_{1-3})$alkyl, $(C_{1-3})$-alkyloxy;
- $(C_{1-4})$alkylcarbonylamino or hydroxyl$(C_{1-3})$alkylaminocarbonyl;
- $R_5$, where present, is H, $(C_{1-4})$alkyl, $(C_{1-4})$alkylcarbonyl or $(C_{1-4})$alkyloxycarbonyl; or a pharmaceutically acceptable salt thereof, with the proviso that N,N-dimethyl-4-bromo-5-phenylisoxazole-3-carboxamide and N,N-diethyl-4-cyano-5-phenylisoxazole-3-carboxamide are excluded.

2. The isoxazole-3-carboxamide derivative of claim 1, wherein the phenyl of $R_1$ is optionally substituted by fluoro, chloro or $CF_3$ or a combination of these.

3. The isoxazole-3-carboxamide derivative of claim 2, wherein $R_2$ is halogen.

4. The isoxazole-3-carboxamide derivative of claim 3, wherein the halogen is Cl or F.

5. The isoxazole-3-carboxamide derivative of claim 1, wherein $R_3$ is tetrahydropyranyl or $(C_{5-6})$cycloalkyl, substituted by hydroxy or hydroxymethyl.

6. An isoxazol-3-carboxamide derivative which is selected from:
- 4-Chloro-5-(4-(trifluoromethyl)phenyl)-N-(3-hydroxyphenyl)isoxazole-3-carboxamide;
- 4-Chloro-5-(4-chlorophenyl)-N-((1R,3S)-3-hydroxycyclohexyl)isoxazole-3-carboxamide;
- 4-Chloro-5-(3,4-difluorophenyl)-N-((1R,3S)-3-hydroxycyclohexyl)isoxazole-3-carboxamide;
- 4-Cyano-N-cyclopentyl-5-(4-(trifluoromethyl)phenyl) isoxazole-3-carboxamide;
- 4-Chloro-N-((1R,3S)-3-hydroxycyclopentyl)-5-(4-(trifluoromethyl)phenyl)isoxazole-3-carboxamide;
- 4-Chloro-N-((1R,3S)-3-hydroxycyclohexyl)-5-(4-(trifluoromethyl)phenyl)isoxazole-3-carboxamide;
- 4-Fluoro-N-((1R,3S)-3-hydroxycyclohexyl)-5-(4-(trifluoromethyl)phenyl)isoxazole-3-carboxamide;
- 4-Chloro-5-(4-chloro-3-fluorophenyl)-N-((1R,3S)-3-hydroxycyclohexyl) isoxazole-3-carboxamide;

4-Chloro-N-cyclopentyl-5-(4-(trifluoromethyl)phenyl) isoxazole-3-carboxamide;
4-Chloro-5-(4-chloro-3-fluorophenyl)-N-((1R,2S)-2-(hydroxymethyl)cyclohexyl) isoxazole-3-carboxamide;
4-Chloro-N-((1S,2R,3S,4R)-3-(hydroxymethyl)bicyclo [2.2.1]heptan-2-yl)-5-(4-(trifluoromethyl)phenyl)isoxazole-3-carboxamide;
4-Bromo-N-(tetrahydro-2H-pyran-4-yl)-5-(4-(trifluoromethyl)phenyl)isoxazole-3-carboxamide;
4-Chloro-N-(tetrahydro-2H-pyran-4-yl)-5-(4-(trifluoromethyl)phenyl)isoxazole-3-carboxamide;
4-Bromo-N-cyclopentyl-5-(4-(trifluoromethyl)phenyl) isoxazole-3-carboxamide;
4-Chloro-N-((1S,2R)-2-(hydroxymethyl)cyclohexyl)-5-(4-(trifluoromethyl)phenyl)isoxazole-3-carboxamide;
4-Chloro-N-((1S,3R)-3-hydroxycyclopentyl)-5-(4-(trifluoromethyl)phenyl) isoxazole-3-carboxamide;
(R)-4-Chloro-N-(3-(hydroxyimino)cyclopentyl)-5-(4-(trifluoromethyl)phenyl) isoxazole-3-carboxamide, cis/trans mix;
Racemic-4-Chloro-N-(cis-2-hydroxycyclohexyl)-5-(4-(trifluoromethyl)phenyl) isoxazole-3-carboxamide;
4-Chloro-5-(4-chloro-3-fluorophenyl)-N-((1R,3S)-3-hydroxycyclopentyl) isoxazole-3-carboxamide;
4-Fluoro-N-((1R,3S)-3-hydroxycyclopentyl)-5-(4-(trifluoromethyl)phenyl) isoxazole-3-carboxamide;
4-Chloro-5-(4-chlorophenyl)-N-((1R,3S)-3-hydroxycyclopentyl)isoxazole-3-carboxamide;
Racemic-cis-4-Chloro-N-(3-hydroxy-6-methoxy-2,3-dihydro-1H-inden-1-yl)-5-(4-(trifluoromethyl)phenyl) isoxazole-3-carboxamide;
4-Chloro-N-(tetrahydro-2H-pyran-3-yl)-5-(4-(trifluoromethyl)phenyl)isoxazole-3-carboxamide;
5-(4-Chlorophenyl)-4-fluoro-N-((1R,3S)-3-hydroxycyclohexyl)isoxazole-3-carboxamide;
(R)-4-Chloro-N-(3-oxocyclopentyl)-5-(4-(trifluoromethyl)phenyl)isoxazole-3-carboxamide;
4-Chloro-N-cyclobutyl-5-(4-(trifluoromethyl)phenyl) isoxazole-3-carboxamide;
4-Methyl-N-(tetrahydro-2H-pyran-4-yl)-5-(4-(trifluoromethyl)phenyl)isoxazole-3-carboxamide;
4-Chloro-N-cyclohexyl-5-(4-(trifluoromethyl)phenyl) isoxazole-3-carboxamide;
4-Chloro-N-((1R,4R)-4-methylcyclohexyl)-5-(4-(trifluoromethyl)phenyl) isoxazole-3-carboxamide;
N-Cyclopentyl-4-methyl-5-(4-(trifluoromethyl)phenyl) isoxazole-3-carboxamide;
4-Chloro-5-(4-chloro-3-fluorophenyl)-N-((1R,3S)-3-hydroxycyclohexyl) isoxazole-3-carboxamide;
Racemic-4-Chloro-N-(cis-2-hydroxycyclohexyl)-5-(4-(trifluoromethyl)phenyl)isoxazole-3-carboxamide;
cis-4-Chloro-N-(4-hydroxycyclohexyl)-5-(4-(trifluoromethyl)phenyl)isoxazole-3-carboxamide;
N-Cyclopentyl-4-propyl-5-(4-(trifluoromethyl)phenyl) isoxazole-3-carboxamide;
N-Cyclopentyl-4-ethyl-5-(4-(trifluoromethyl)phenyl) isoxazole-3-carboxamide;
4-Chloro-5-(4-chlorophenyl)-N-cyclopentylisoxazole-3-carboxamide;
(S)-4-Chloro-N-(3-methylbutan-2-yl)-5-(4-(trifluoromethyl)phenyl)isoxazole-3-carboxamide;
4-Chloro-5-(3-fluoro-4-(trifluoromethyl)phenyl)-N-(tetrahydro-2H-pyran-4-yl)isoxazole-3-carboxamide;
4-Chloro-5-(3-fluoro-4-(trifluoromethyl)phenyl)-N-(tetrahydro-2H-pyran-4-yl)isoxazole-3-carboxamide;
4-Chloro-5-(3-fluoro-4-(trifluoromethyl)phenyl)-N-(3-(hydroxymethyl)phenyl) isoxazole-3-carboxamide;
4-Chloro-5-(3-fluoro-4-(trifluoromethyl)phenyl)-N-(2-(2-hydroxyethyl)phenyl) isoxazole-3-carboxamide;
(R)-4-Chloro-5-(3-fluoro-4-(trifluoromethyl)phenyl)-N-(1-hydroxybutan-2-yl)isoxazole-3-carboxamide;
(R)-4-Chloro-5-(3-fluoro-4-(trifluoromethyl)phenyl)-N-(1-hydroxy-3-methylbutan-2-yl)isoxazole-3-carboxamide;
4-Chloro-5-(3-fluoro-4-(trifluoromethyl)phenyl)-N-((1R,3S)-3-hydroxycyclohexyl)-isoxazole-3-carboxamide;
cis-4-Chloro-5-(3-fluoro-4-(trifluoromethyl)phenyl)-N-(4-hydroxycyclohexyl) isoxazole-3-carboxamide;
4-Chloro-5-(4-chlorophenyl)-N-cyclohexylisoxazole-3-carboxamide;
4-Chloro-5-(4-chlorophenyl)-N-cyclobutylisoxazole-3-carboxamide;
5-(4-tert-Butylphenyl)-4-chloro-N-cyclopentylisoxazole-3-carboxamide;
5-(4-tert-Butylphenyl)-4-chloro-N-(cis-4-hydroxycyclohexyl)isoxazole-3-carboxamide;
5-(4-tert-Butylphenyl)-4-chloro-N-((1S,2R)-2-(hydroxymethyl)cyclohexyl)isoxazole-3-carboxamide;
5-(4-tert-Butylphenyl)-4-chloro-N-(tetrahydro-2H-pyran-4-yl)isoxazole-3-carboxamide;
5-(4-tert-Butylphenyl)-4-chloro-N-cyclobutylisoxazole-3-carboxamide 2,2,2-trifluoroacetate;
5-(4-tert-Butylphenyl)-4-chloro-N-isopropylisoxazole-3-carboxamide 2,2,2-trifluoroacetate;
(S)-4-Chloro-5-(4-(trifluoromethyl)phenyl)-N-(1,1,1-trifluoropropan-2-yl)isoxazole-3-carboxamide;
(R)—N-sec-Butyl-4-chloro-5-(4-(trifluoromethyl)phenyl)isoxazole-3-carboxamide;
4-Chloro-N-(cyclobutylmethyl)-5-(4-(trifluoromethyl) phenyl)isoxazole-3-carboxamide;
4-Chloro-N-(2-cyclopropylethyl)-5-(4-(trifluoromethyl) phenyl)isoxazole-3-carboxamide;
4-Chloro-N-(1,1,1-trifluorobutan-2-yl)-5-(4-(trifluoromethyl)phenyl)isoxazole-3-carboxamide;
4-Chloro-N-(3,3-difluorocyclobutyl)-5-(4-(trifluoromethyl)phenyl)isoxazole-3-carboxamide;
5-(4-Chloro-2-ethoxyphenyl)-N-((1R,2S)-2-hydroxycyclohexyl)-4-methylisoxazole-3-carboxamide;
5-(3-Fluoro-4-(trifluoromethyl)phenyl)-4-methyl-N-(tetrahydro-2H-pyran-4-yl)isoxazole-3-carboxamide;
5-(3-Fluoro-4-(trifluoromethyl)phenyl)-N-((1R,3S)-3-hydroxycyclohexyl)-4-methylisoxazole-3-carboxamide;
5-(3-Fluoro-4-(trifluoromethyl)phenyl)-N-(2-hydroxyethyl)-4-methylisoxazole-3-carboxamide;
(R)-5-(3-Fluoro-4-(trifluoromethyl)phenyl)-N-(1-hydroxybutan-2-yl)-4-methylisoxazole-3-carboxamide;
5-(4-Chloro-2-ethoxyphenyl)-N-((1R,3S)-3-hydroxycyclohexyl)-4-methylisoxazole-3-carboxamide;
Racemic-5-(4-Chloro-2-ethoxyphenyl)-N-(cis-2-hydroxycyclohexyl)-4-methylisoxazole-3-carboxamide;
(R)-4-Chloro-N-(tetrahydrofuran-3-yl)-5-(4-(trifluoromethyl)phenyl)isoxazole-3-carboxamide;
4-Chloro-N-((1R,2S)-2-hydroxycyclopentyl)-5-(4-(trifluoromethyl)phenyl)isoxazole-3-carboxamide;
(R)-4-Chloro-5-(3-fluoro-4-(trifluoromethyl)phenyl)-N-(tetrahydrofuran-3-yl)isoxazole-3-carboxamide;
4-Chloro-5-(3-fluoro-4-(trifluoromethyl)phenyl)-N-((1R,2S)-2-hydroxycyclopentyl)-isoxazole-3-carboxamide;
N-Cyclopentyl-5-(3-fluoro-4-(trifluoromethyl)phenyl)-4-methylisoxazole-3-carboxamide;
5-(4-Chloro-2-ethoxyphenyl)-4-methyl-N—((S)-1,1,1-trifluoropropan-2-yl)isoxazole-3-carboxamide;
5-(4-Chloro-2-ethoxyphenyl)-N-(3,3-difluorocyclobutyl)-4-methylisoxazole-3-carboxamide;

(S)-5-(3-Fluoro-4-(trifluoromethyl)phenyl)-4-methyl-N-(3-methylbutan-2-yl)isoxazole-3-carboxamide;
4-Chloro-N-isopropyl-5-(4-(trifluoromethyl)phenyl)isoxazole-3-carboxamide;
N-(3,3-Difluorocyclobutyl)-5-(3-fluoro-4-(trifluoromethyl)phenyl)-4-methylisoxazole-3-carboxamide;
(R)-5-(3-Fluoro-4-(trifluoromethyl)phenyl)-N-(1-hydroxy-3-methylbutan-2-yl)-4-methylisoxazole-3-carboxamide;
4-Chloro-5-(4-chlorophenyl)-N-(cyclopropylmethyl)isoxazole-3-carboxamide;
4-Bromo-5-[4-(trifluoromethyl)phenyl]-N-(cyclopropylmethyl)isoxazole-3-carboxamide; or a pharmaceutically acceptable salt thereof.

7. A pharmaceutical composition comprising the isoxazole-3-carboxamide derivative of claim 1 or a pharmaceutically acceptable salt thereof and pharmaceutically suitable auxiliaries.

8. A pharmaceutical composition comprising the isoxazole-3-carboxamide derivative of claim 6 or a pharmaceutically acceptable salt thereof and pharmaceutically suitable auxiliaries.

9. A pharmaceutical composition comprising N,N-dimethyl-4-bromo-5-phenylisoxazole-3-carboxamide or a pharmaceutically acceptable salt thereof and pharmaceutically suitable auxiliaries.

10. A pharmaceutical composition comprising N,N-diethyl-4-cyano-5-phenyl-isoxazole-3-carboxamide or a pharmaceutically acceptable salt thereof and pharmaceutically suitable auxiliaries.

11. A method for the treatment of TRPV1 mediated disorders selected from the group consisting of acute and chronic pain disorders, acute and chronic neuropathic pain, acute and chronic inflammatory pain comprising administering an isoxazole-3-carboxamide derivative of claim 6.

12. A method for the treatment of TRPV1 mediated disorders selected from the group consisting of acute and chronic pain disorders, acute and chronic neuropathic pain, acute and chronic inflammatory pain comprising administering N,N-dimethyl-4-bromo-5-phenylisoxazole-3-carboxamide or a pharmaceutically acceptable salt thereof.

13. A method for the treatment of TRPV1 mediated disorders selected from the group consisting of acute and chronic pain disorders, acute and chronic neuropathic pain, acute and chronic inflammatory pain comprising administering N,N-diethyl-4-cyano-5-phenylisoxazole-3-carboxamide or a pharmaceutically acceptable salt thereof.

* * * * *